US008696549B2

(12) United States Patent
Holsing et al.

(10) Patent No.: US 8,696,549 B2
(45) Date of Patent: Apr. 15, 2014

(54) APPARATUS AND METHOD FOR FOUR DIMENSIONAL SOFT TISSUE NAVIGATION IN ENDOSCOPIC APPLICATIONS

(75) Inventors: Troy Holsing, Boulder, CO (US); Mark Hunter, St. Louis, MO (US)

(73) Assignee: Veran Medical Technologies, Inc., St. Louis, MO (US)

( * ) Notice: Subject to any disclaimer, the term of this patent is extended or adjusted under 35 U.S.C. 154(b) by 4 days.

(21) Appl. No.: 13/215,017

(22) Filed: Aug. 22, 2011

(65) Prior Publication Data

US 2012/0059220 A1 Mar. 8, 2012

Related U.S. Application Data

(60) Provisional application No. 61/375,439, filed on Aug. 20, 2010, provisional application No. 61/375,484, filed on Aug. 20, 2010, provisional application No. 61/375,523, filed on Aug. 20, 2010, provisional application No. 61/375,533, filed on Aug. 20, 2010.

(51) Int. Cl.
*A61B 1/005* (2006.01)
*A61B 1/04* (2006.01)

(52) U.S. Cl.
USPC ............................ 600/117; 600/103; 600/146

(58) Field of Classification Search
USPC ......................................... 600/103, 117, 146
See application file for complete search history.

(56) References Cited

U.S. PATENT DOCUMENTS

| 3,788,324 | A | 1/1974 | Lim |
|---|---|---|---|
| 4,421,106 | A | 12/1983 | Uehara |
| 4,583,538 | A | 4/1986 | Onik et al. |
| 5,053,042 | A | 10/1991 | Bidwell |
| 5,158,088 | A | 10/1992 | Nelson et al. |
| 5,186,174 | A | 2/1993 | Schlondorff et al. |
| 5,251,165 | A | 10/1993 | James, III |
| 5,251,635 | A | 10/1993 | Dumoulin et al. |

(Continued)

FOREIGN PATENT DOCUMENTS

| DE | 19725137 | 1/1999 |
|---|---|---|
| DE | 19829224 | 1/2000 |

(Continued)

OTHER PUBLICATIONS

Patent Cooperation Treat, International Search Report and Written Opinion from PCT/US06/35548, mailed Aug. 20, 2007, 7 pages.

(Continued)

*Primary Examiner* — John P Leubecker
(74) *Attorney, Agent, or Firm* — Bryan Cave LLP

(57) ABSTRACT

A surgical instrument navigation system is provided that visually simulates a virtual volumetric scene of a body cavity of a patient from a point of view of a surgical instrument residing in the cavity of the patient. The surgical instrument navigation system includes: a surgical instrument; an imaging device which is operable to capture scan data representative of an internal region of interest within a given patient; a tracking subsystem that employs electro-magnetic sensing to capture in real-time position data indicative of the position of the surgical instrument; a data processor which is operable to render a volumetric, perspective image of the internal region of interest from a point of view of the surgical instrument; and a display which is operable to display the volumetric perspective image of the patient.

5 Claims, 21 Drawing Sheets

(56) References Cited

U.S. PATENT DOCUMENTS

| | | | |
|---|---|---|---|
| 5,265,610 | A | 11/1993 | Darrow et al. |
| 5,348,011 | A | 9/1994 | NessAiver |
| 5,377,678 | A | 1/1995 | Dumoulin et al. |
| 5,391,199 | A | 2/1995 | Ben-Haim |
| 5,437,292 | A | 8/1995 | Kipshidze et al. |
| 5,483,691 | A | 1/1996 | Heck et al. |
| 5,483,961 | A | 1/1996 | Kelly et al. |
| 5,577,502 | A | 11/1996 | Darrow et al. |
| 5,581,183 | A | 12/1996 | Lindstedt et al. |
| 5,644,612 | A | 7/1997 | Moorman et al. |
| 5,671,739 | A | 9/1997 | Darrow et al. |
| 5,718,241 | A | 2/1998 | Ben-Haim et al. |
| 5,730,129 | A | 3/1998 | Darrow et al. |
| 5,740,808 | A | 4/1998 | Panescu et al. |
| 5,765,561 | A | 6/1998 | Chen et al. |
| 5,769,789 | A | 6/1998 | Wang et al. |
| 5,769,861 | A | 6/1998 | Vilsmeier |
| 5,771,306 | A | 6/1998 | Stork et al. |
| 5,787,886 | A | 8/1998 | Kelly et al. |
| 5,803,089 | A | 9/1998 | Ferre et al. |
| 5,814,022 | A | 9/1998 | Antanavich et al. |
| 5,814,066 | A | 9/1998 | Spotnitz |
| 5,833,608 | A * | 11/1998 | Acker ............ 600/409 |
| 5,840,025 | A | 11/1998 | Ben-Haim |
| 5,868,673 | A | 2/1999 | Vesely |
| 5,928,248 | A * | 7/1999 | Acker ............ 623/1.11 |
| 5,978,696 | A | 11/1999 | VomLehn et al. |
| 6,016,439 | A * | 1/2000 | Acker ............ 600/411 |
| 6,019,724 | A | 2/2000 | Gronningsaeter et al. |
| 6,026,173 | A | 2/2000 | Svenson et al. |
| 6,078,175 | A | 6/2000 | Foo |
| 6,122,538 | A | 9/2000 | Sliwa, Jr. et al. |
| 6,122,541 | A | 9/2000 | Cosman et al. |
| 6,132,396 | A | 10/2000 | Antanavich et al. |
| 6,144,875 | A | 11/2000 | Schweikard et al. |
| 6,167,296 | A | 12/2000 | Shahidi |
| 6,173,201 | B1 | 1/2001 | Front |
| 6,198,959 | B1 | 3/2001 | Wang |
| 6,201,987 | B1 | 3/2001 | Dumoulin |
| 6,226,543 | B1 | 5/2001 | Gilboa et al. |
| 6,226,548 | B1 | 5/2001 | Foley et al. |
| 6,233,476 | B1 | 5/2001 | Strommer et al. |
| 6,235,038 | B1 | 5/2001 | Hunter et al. |
| 6,236,875 | B1 | 5/2001 | Bucholz et al. |
| 6,246,896 | B1 | 6/2001 | Dumoulin et al. |
| 6,246,898 | B1 | 6/2001 | Vesely et al. |
| 6,253,770 | B1 * | 7/2001 | Acker et al. ............ 128/899 |
| 6,267,769 | B1 | 7/2001 | Truwit |
| 6,275,560 | B1 | 8/2001 | Blake et al. |
| 6,282,442 | B1 | 8/2001 | DeStefano et al. |
| 6,285,902 | B1 | 9/2001 | Kienzle, III et al. |
| 6,298,259 | B1 | 10/2001 | Kucharczyk et al. |
| 6,314,310 | B1 | 11/2001 | Ben-Haim et al. |
| 6,314,311 | B1 | 11/2001 | Williams et al. |
| 6,314,312 | B1 | 11/2001 | Wessels et al. |
| 6,317,616 | B1 | 11/2001 | Glossop |
| 6,317,619 | B1 | 11/2001 | Boernert et al. |
| 6,330,356 | B1 | 12/2001 | Sundareswaran et al. |
| 6,332,089 | B1 | 12/2001 | Acker et al. |
| 6,332,891 | B1 | 12/2001 | Himes |
| 6,335,617 | B1 | 1/2002 | Osadchy et al. |
| 6,335,623 | B1 | 1/2002 | Damadian et al. |
| 6,340,363 | B1 | 1/2002 | Bolger et al. |
| 6,347,240 | B1 | 2/2002 | Foley et al. |
| 6,348,058 | B1 | 2/2002 | Melkent et al. |
| 6,351,573 | B1 | 2/2002 | Schneider |
| 6,351,659 | B1 | 2/2002 | Vilsmeier |
| 6,361,759 | B1 | 3/2002 | Frayne et al. |
| 6,362,821 | B1 | 3/2002 | Gibson et al. |
| 6,368,331 | B1 | 4/2002 | Front |
| 6,369,571 | B1 | 4/2002 | Damadian et al. |
| 6,373,998 | B2 * | 4/2002 | Thirion et al. ............ 382/294 |
| 6,379,302 | B1 | 4/2002 | Kessman et al. |
| 6,381,485 | B1 | 4/2002 | Hunter et al. |
| 6,402,762 | B2 | 6/2002 | Hunter et al. |
| 6,418,238 | B1 | 7/2002 | Shiratani et al. |
| 6,421,551 | B1 | 7/2002 | Kuth et al. |
| 6,424,856 | B1 | 7/2002 | Vilsmeier et al. |
| 6,425,865 | B1 | 7/2002 | Salcudean et al. |
| 6,430,430 | B1 | 8/2002 | Gosche |
| 6,434,415 | B1 | 8/2002 | Foley et al. |
| 6,434,507 | B1 | 8/2002 | Clayton et al. |
| 6,437,571 | B1 | 8/2002 | Danby et al. |
| 6,442,417 | B1 | 8/2002 | Shahidi et al. |
| 6,445,186 | B1 | 9/2002 | Damadian et al. |
| 6,445,943 | B1 | 9/2002 | Ferre et al. |
| 6,455,182 | B1 | 9/2002 | Silver |
| 6,461,372 | B1 | 10/2002 | Jensen et al. |
| 6,468,265 | B1 | 10/2002 | Evans et al. |
| 6,469,508 | B1 | 10/2002 | Damadian et al. |
| 6,470,066 | B2 | 10/2002 | Takagi et al. |
| 6,470,207 | B1 | 10/2002 | Simon et al. |
| 6,473,635 | B1 | 10/2002 | Rasche |
| 6,477,400 | B1 | 11/2002 | Barrick |
| 6,478,793 | B1 | 11/2002 | Cosman et al. |
| 6,478,802 | B2 | 11/2002 | Kienzle, III et al. |
| 6,483,948 | B1 | 11/2002 | Spink et al. |
| 6,484,049 | B1 | 11/2002 | Seeley et al. |
| 6,485,413 | B1 | 11/2002 | Boppart et al. |
| D466,609 | S | 12/2002 | Glossop |
| D466,610 | S | 12/2002 | Ashton et al. |
| 6,490,467 | B1 | 12/2002 | Bucholz et al. |
| 6,490,475 | B1 | 12/2002 | Seeley et al. |
| 6,490,477 | B1 | 12/2002 | Zylka et al. |
| 6,491,699 | B1 | 12/2002 | Henderson et al. |
| 6,491,702 | B2 | 12/2002 | Heilbrun et al. |
| 6,493,574 | B1 | 12/2002 | Ehnholm et al. |
| 6,496,007 | B1 | 12/2002 | Damadian et al. |
| 6,501,981 | B1 | 12/2002 | Schweikard et al. |
| 6,504,893 | B1 | 1/2003 | Flohr et al. |
| 6,504,894 | B2 | 1/2003 | Pan et al. |
| 6,517,485 | B2 | 2/2003 | Torp et al. |
| 6,527,443 | B1 | 3/2003 | Vilsmeier et al. |
| 6,535,756 | B1 | 3/2003 | Simon et al. |
| 6,538,634 | B1 | 3/2003 | Chui et al. |
| 6,539,127 | B1 | 3/2003 | Roche et al. |
| 6,541,973 | B1 | 4/2003 | Danby et al. |
| 6,544,041 | B1 | 4/2003 | Damadian |
| 6,547,782 | B1 | 4/2003 | Taylor |
| 6,558,333 | B2 | 5/2003 | Gilboa et al. |
| 6,562,059 | B2 | 5/2003 | Edwards et al. |
| 6,567,687 | B2 | 5/2003 | Front et al. |
| 6,580,938 | B1 | 6/2003 | Acker |
| 6,584,174 | B2 | 6/2003 | Schubert et al. |
| 6,584,339 | B2 | 6/2003 | Galloway, Jr. et al. |
| 6,591,130 | B2 | 7/2003 | Shahidi |
| 6,606,513 | B2 | 8/2003 | Lardo et al. |
| 6,609,022 | B2 | 8/2003 | Vilsmeier et al. |
| 6,636,757 | B1 | 10/2003 | Jascob et al. |
| 6,650,924 | B2 | 11/2003 | Kuth et al. |
| 6,666,579 | B2 | 12/2003 | Jensen |
| 6,674,833 | B2 | 1/2004 | Shahidi et al. |
| 6,675,032 | B2 | 1/2004 | Chen et al. |
| 6,675,033 | B1 | 1/2004 | Lardo et al. |
| 6,687,531 | B1 | 2/2004 | Ferre et al. |
| 6,690,960 | B2 | 2/2004 | Chen et al. |
| 6,694,167 | B1 | 2/2004 | Ferre et al. |
| 6,697,664 | B2 | 2/2004 | Kienzle III et al. |
| 6,711,429 | B1 | 3/2004 | Gilboa et al. |
| 6,714,629 | B2 | 3/2004 | Vilsmeier |
| 6,714,810 | B2 | 3/2004 | Grzeszczuk et al. |
| 6,725,080 | B2 | 4/2004 | Melkent et al. |
| 6,738,656 | B1 | 5/2004 | Ferre et al. |
| 6,774,624 | B2 | 8/2004 | Anderson et al. |
| 6,782,287 | B2 | 8/2004 | Grzeszczuk et al. |
| 6,796,988 | B2 | 9/2004 | Estes et al. |
| 6,799,569 | B2 | 10/2004 | Danielsson et al. |
| 6,823,207 | B1 | 11/2004 | Jensen et al. |
| 6,826,423 | B1 | 11/2004 | Hardy et al. |
| 6,850,794 | B2 | 2/2005 | Shahidi |
| 6,856,826 | B2 | 2/2005 | Seeley et al. |
| 6,856,827 | B2 | 2/2005 | Seeley et al. |
| 6,892,090 | B2 | 5/2005 | Verard et al. |
| 6,898,303 | B2 | 5/2005 | Armato, III et al. |

(56) References Cited

U.S. PATENT DOCUMENTS

| | | | |
|---|---|---|---|
| 6,899,672 B2* | 5/2005 | Chin et al. | 600/121 |
| 6,907,281 B2 | 6/2005 | Grzeszczuk | |
| 6,920,347 B2 | 7/2005 | Simon et al. | |
| 6,925,200 B2 | 8/2005 | Wood et al. | |
| 6,934,575 B2 | 8/2005 | Ferre et al. | |
| 6,968,224 B2 | 11/2005 | Kessman et al. | |
| 6,978,166 B2 | 12/2005 | Foley et al. | |
| 6,992,477 B2 | 1/2006 | Govari | |
| 7,015,859 B2 | 3/2006 | Anderson | |
| 7,015,907 B2 | 3/2006 | Tek et al. | |
| 7,050,845 B2 | 5/2006 | Vilsmeier | |
| 7,139,601 B2 | 11/2006 | Bucholz et al. | |
| 7,153,297 B2 | 12/2006 | Peterson | |
| 7,171,257 B2 | 1/2007 | Thomson | |
| 7,174,201 B2 | 2/2007 | Govari et al. | |
| 7,260,426 B2 | 8/2007 | Schweikard et al. | |
| 7,366,562 B2 | 4/2008 | Dukesherer et al. | |
| 7,398,116 B2 | 7/2008 | Edwards | |
| 7,505,806 B2 | 3/2009 | Masutani et al. | |
| 7,599,730 B2 | 10/2009 | Hunter et al. | |
| 7,697,972 B2 | 4/2010 | Verard et al. | |
| 7,933,380 B2* | 4/2011 | Nord et al. | 378/65 |
| 8,046,052 B2 | 10/2011 | Verard et al. | |
| 8,298,135 B2* | 10/2012 | Ito et al. | 600/117 |
| 8,483,801 B2 | 7/2013 | Edwards | |
| 2001/0007918 A1 | 7/2001 | Vilsmeier et al. | |
| 2001/0025142 A1 | 9/2001 | Wessels et al. | |
| 2001/0029333 A1 | 10/2001 | Shahidi | |
| 2001/0031919 A1 | 10/2001 | Strommer et al. | |
| 2001/0031985 A1 | 10/2001 | Gilboa et al. | |
| 2001/0036245 A1 | 11/2001 | Kienzle et al. | |
| 2001/0041835 A1 | 11/2001 | Front et al. | |
| 2002/0044631 A1 | 4/2002 | Graumann et al. | |
| 2002/0049375 A1 | 4/2002 | Strommer et al. | |
| 2002/0049378 A1 | 4/2002 | Grzeszczuk et al. | |
| 2002/0070970 A1 | 6/2002 | Wood et al. | |
| 2002/0075994 A1 | 6/2002 | Shahidi et al. | |
| 2002/0077543 A1 | 6/2002 | Grzeszczuk et al. | |
| 2002/0077544 A1 | 6/2002 | Shahidi | |
| 2002/0082492 A1 | 6/2002 | Grzeszczuk | |
| 2002/0085681 A1 | 7/2002 | Jensen | |
| 2002/0143317 A1 | 10/2002 | Glossop | |
| 2002/0161295 A1 | 10/2002 | Edwards et al. | |
| 2003/0000535 A1 | 1/2003 | Galloway, Jr. et al. | |
| 2003/0004411 A1 | 1/2003 | Govari et al. | |
| 2003/0016852 A1 | 1/2003 | Kaufman et al. | |
| 2003/0018251 A1 | 1/2003 | Solomon | |
| 2003/0023161 A1 | 1/2003 | Govari et al. | |
| 2003/0028091 A1 | 2/2003 | Simon et al. | |
| 2003/0029464 A1 | 2/2003 | Chen et al. | |
| 2003/0032878 A1 | 2/2003 | Shahidi | |
| 2003/0040667 A1 | 2/2003 | Feussner et al. | |
| 2003/0074011 A1 | 4/2003 | Gilboa et al. | |
| 2003/0088179 A1 | 5/2003 | Seeley et al. | |
| 2003/0125622 A1 | 7/2003 | Schweikard et al. | |
| 2003/0130576 A1 | 7/2003 | Seeley et al. | |
| 2003/0139663 A1 | 7/2003 | Graumann | |
| 2003/0199785 A1 | 10/2003 | Hibner et al. | |
| 2003/0208116 A1 | 11/2003 | Liang et al. | |
| 2003/0208122 A1 | 11/2003 | Melkent et al. | |
| 2003/0216631 A1 | 11/2003 | Bloch et al. | |
| 2003/0220557 A1 | 11/2003 | Cleary et al. | |
| 2004/0006268 A1 | 1/2004 | Gilboa et al. | |
| 2004/0034300 A1 | 2/2004 | Verard et al. | |
| 2004/0049121 A1 | 3/2004 | Yaron | |
| 2004/0076259 A1 | 4/2004 | Jensen et al. | |
| 2004/0092815 A1 | 5/2004 | Schweikard et al. | |
| 2004/0097805 A1 | 5/2004 | Verard et al. | |
| 2004/0097806 A1 | 5/2004 | Hunter et al. | |
| 2004/0116803 A1 | 6/2004 | Jascob et al. | |
| 2004/0122311 A1 | 6/2004 | Cosman | |
| 2004/0138548 A1 | 7/2004 | Strommer et al. | |
| 2004/0152970 A1 | 8/2004 | Hunter et al. | |
| 2004/0152974 A1 | 8/2004 | Solomon | |
| 2004/0167393 A1 | 8/2004 | Solar et al. | |
| 2004/0193042 A1 | 9/2004 | Scampini et al. | |
| 2004/0210125 A1 | 10/2004 | Chen et al. | |
| 2004/0249267 A1 | 12/2004 | Gilboa | |
| 2005/0010099 A1 | 1/2005 | Raabe et al. | |
| 2005/0027186 A1 | 2/2005 | Chen et al. | |
| 2005/0033149 A1 | 2/2005 | Strommer et al. | |
| 2005/0038337 A1 | 2/2005 | Edwards | |
| 2005/0065433 A1 | 3/2005 | Anderson et al. | |
| 2005/0085718 A1* | 4/2005 | Shahidi | 600/424 |
| 2005/0085793 A1 | 4/2005 | Glossop | |
| 2005/0107679 A1 | 5/2005 | Geiger et al. | |
| 2005/0107688 A1 | 5/2005 | Strommer | |
| 2005/0113809 A1 | 5/2005 | Melkent et al. | |
| 2005/0143651 A1 | 6/2005 | Verard et al. | |
| 2005/0169510 A1 | 8/2005 | Zuhars et al. | |
| 2005/0182295 A1 | 8/2005 | Soper et al. | |
| 2005/0182319 A1 | 8/2005 | Glossop | |
| 2005/0187482 A1 | 8/2005 | O'Brien et al. | |
| 2005/0197568 A1 | 9/2005 | Vass et al. | |
| 2005/0203383 A1 | 9/2005 | Moctezuma de la Barrera et al. | |
| 2005/0234335 A1 | 10/2005 | Simon et al. | |
| 2005/0288574 A1 | 12/2005 | Thornton et al. | |
| 2005/0288578 A1 | 12/2005 | Durlak | |
| 2006/0004281 A1 | 1/2006 | Saracen | |
| 2006/0025677 A1 | 2/2006 | Verard et al. | |
| 2006/0045318 A1 | 3/2006 | Schoisswohl et al. | |
| 2006/0050942 A1 | 3/2006 | Bertram et al. | |
| 2006/0050988 A1 | 3/2006 | Kraus et al. | |
| 2006/0058647 A1 | 3/2006 | Strommer et al. | |
| 2006/0063998 A1 | 3/2006 | von Jako et al. | |
| 2006/0064006 A1 | 3/2006 | Strommer et al. | |
| 2006/0074292 A1 | 4/2006 | Thomson et al. | |
| 2006/0074299 A1 | 4/2006 | Sayeh | |
| 2006/0074304 A1 | 4/2006 | Sayeh | |
| 2006/0079759 A1 | 4/2006 | Vaillant et al. | |
| 2006/0084867 A1 | 4/2006 | Tremblay et al. | |
| 2006/0093089 A1 | 5/2006 | Vertatschitsch et al. | |
| 2006/0094958 A1 | 5/2006 | Marquart et al. | |
| 2006/0106292 A1 | 5/2006 | Anderson | |
| 2006/0116634 A1 | 6/2006 | Shachar | |
| 2006/0122497 A1 | 6/2006 | Glossop | |
| 2006/0142798 A1 | 6/2006 | Holman et al. | |
| 2006/0173269 A1 | 8/2006 | Glossop | |
| 2006/0173291 A1 | 8/2006 | Glossop | |
| 2006/0189867 A1 | 8/2006 | Revie et al. | |
| 2006/0247511 A1 | 11/2006 | Anderson | |
| 2007/0032723 A1 | 2/2007 | Glossop | |
| 2007/0038058 A1 | 2/2007 | West et al. | |
| 2007/0066887 A1 | 3/2007 | Mire et al. | |
| 2007/0110289 A1 | 5/2007 | Fu et al. | |
| 2007/0129629 A1 | 6/2007 | Beauregard et al. | |
| 2007/0167744 A1 | 7/2007 | Beauregard et al. | |
| 2007/0225559 A1* | 9/2007 | Clerc et al. | 600/117 |
| 2007/0244355 A1 | 10/2007 | Shaw | |
| 2007/0249896 A1 | 10/2007 | Goldfarb et al. | |
| 2008/0071143 A1* | 3/2008 | Gattani et al. | 600/117 |
| 2008/0132757 A1* | 6/2008 | Tgavalekos | 600/104 |
| 2008/0140114 A1 | 6/2008 | Edwards et al. | |
| 2008/0247622 A1 | 10/2008 | Aylward et al. | |
| 2008/0269561 A1 | 10/2008 | Banik et al. | |
| 2008/0287803 A1 | 11/2008 | Li et al. | |
| 2009/0156895 A1* | 6/2009 | Higgins et al. | 600/104 |
| 2009/0227861 A1 | 9/2009 | Ganatra et al. | |
| 2010/0041949 A1* | 2/2010 | Tolkowsky | 600/109 |
| 2010/0160733 A1* | 6/2010 | Gilboa | 600/117 |
| 2010/0249506 A1* | 9/2010 | Prisco | 600/117 |
| 2011/0282151 A1* | 11/2011 | Trovato et al. | 600/117 |
| 2012/0059248 A1 | 3/2012 | Holsing et al. | |
| 2012/0123296 A1 | 5/2012 | Hashimshony et al. | |

FOREIGN PATENT DOCUMENTS

| | | |
|---|---|---|
| DE | 19909816 | 5/2000 |
| DE | 199909816 | 5/2000 |
| DE | 100000937 | 8/2001 |
| DE | 10136709 | 2/2003 |
| DE | 10161160 | 6/2003 |
| DE | 102005010010 | 9/2005 |
| DE | 102004030836 | 1/2006 |

(56) References Cited

FOREIGN PATENT DOCUMENTS

| | | |
|---|---|---|
| DE | 102005038394 | 3/2006 |
| DE | 102005050286 | 4/2006 |
| DE | 102004058122 | 7/2006 |
| EP | 0501993 | 9/1992 |
| EP | 0869745 | 10/1998 |
| EP | 900048 | 3/1999 |
| EP | 0928600 | 7/1999 |
| EP | 977510 | 2/2000 |
| EP | 1079240 | 2/2001 |
| EP | 1152706 | 11/2001 |
| EP | 1181897 | 2/2002 |
| EP | 1319368 | 6/2003 |
| EP | 1374792 | 1/2004 |
| EP | 1374793 | 1/2004 |
| EP | 1391181 | 2/2004 |
| EP | 1421913 | 5/2004 |
| EP | 1464285 | 10/2004 |
| EP | 1504713 | 2/2005 |
| EP | 1504726 | 2/2005 |
| EP | 1519140 | 3/2005 |
| EP | 1523951 | 4/2005 |
| EP | 1561423 | 8/2005 |
| EP | 1629774 | 3/2006 |
| EP | 1629789 | 3/2006 |
| EP | 2380550 | 10/2011 |
| FR | 2876273 | 4/2006 |
| WO | 9424933 | 11/1994 |
| WO | 9501757 | 1/1995 |
| WO | 9608209 | 3/1996 |
| WO | 9610949 | 4/1996 |
| WO | 9626672 | 9/1996 |
| WO | 9729699 | 8/1997 |
| WO | 9729709 | 8/1997 |
| WO | 9836684 | 8/1998 |
| WO | 9916352 | 4/1999 |
| WO | 9927839 | 6/1999 |
| WO | 9943253 | 9/1999 |
| WO | 0016684 | 3/2000 |
| WO | 0028911 | 5/2000 |
| WO | 0047103 | 8/2000 |
| WO | 0049958 | 8/2000 |
| WO | 0057767 | 10/2000 |
| WO | 0069335 | 11/2000 |
| WO | 0101845 | 1/2001 |
| WO | 0137748 | 5/2001 |
| WO | 0162134 | 8/2001 |
| WO | 0164124 | 9/2001 |
| WO | 0176496 | 10/2001 |
| WO | 0176497 | 10/2001 |
| WO | 0187136 | 11/2001 |
| WO | 0193745 | 12/2001 |
| WO | 0200093 | 1/2002 |
| WO | 0200103 | 1/2002 |
| WO | 0219936 | 3/2002 |
| WO | 0222015 | 3/2002 |
| WO | 0224051 | 3/2002 |
| WO | 02056770 | 7/2002 |
| WO | 02064011 | 8/2002 |
| WO | 02082375 | 10/2002 |
| WO | 02098273 | 12/2002 |
| WO | 2004046754 | 6/2004 |
| WO | 2004060157 | 7/2004 |
| WO | 2004062497 | 7/2004 |
| WO | 2005016166 | 2/2005 |
| WO | 2005070318 | 8/2005 |
| WO | 2005077293 | 10/2005 |
| WO | 2005101277 | 10/2005 |
| WO | 2005111942 | 11/2005 |
| WO | 2006002396 | 1/2006 |
| WO | 2006005021 | 1/2006 |
| WO | 2006027781 | 3/2006 |
| WO | 2006039009 | 4/2006 |
| WO | 2006051523 | 5/2006 |
| WO | 2006090141 | 8/2006 |
| WO | 2007002079 | 1/2007 |
| WO | 2007031314 | 3/2007 |
| WO | 2007033206 | 3/2007 |
| WO | 2007062051 | 5/2007 |
| WO | 2007084893 | 7/2007 |
| WO | 2009158578 | 12/2009 |

OTHER PUBLICATIONS

New Navigational Aid Could Improve hip replacement outcomes, Medical Industry Today, Jul. 11, 1997, 2 pages Jul. 11, 1997.
Highlights from Presentation of 5th Joint Meeting of European Assn. for Cardio-Thoracic Surgery and European Society of Thoracic Surgeons "Evidence for Fleece-Bound Sealants in Cardiothoracic Surgery" Sep. 9-13, 2006 Sep. 9, 2006.
Moore, E. et al., Needle Aspiration Lung Biopsy: Re-evaluation of the blood patch technique in an equine model, Radiology, 196(1) Jul. 1, 1995.
FDA Approves Lung Sealant, May 31, 2000 [online], [retrieved Oct. 17, 2008 from Internet]; http://www.meds.com/archive/mol-cancer/2000/05/msg01329.html Aug. 31, 2000.
Patent Cooperation Treat, International Search Report from PCT/US11/48669, mailed Apr. 9, 2012, 7 pages.

* cited by examiner

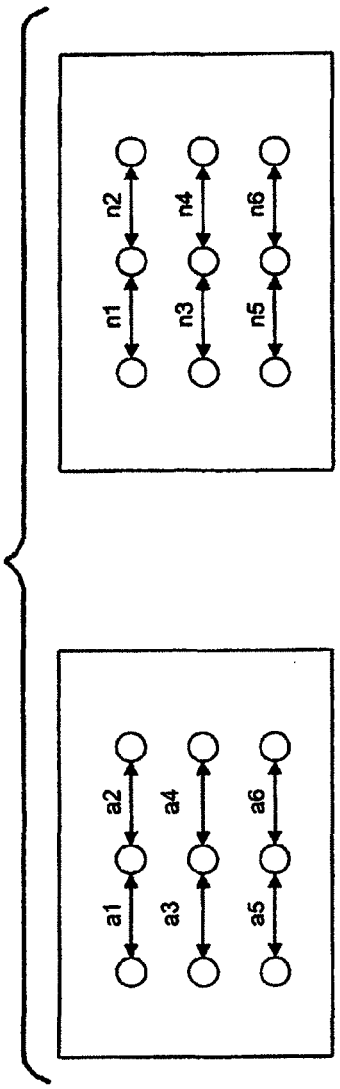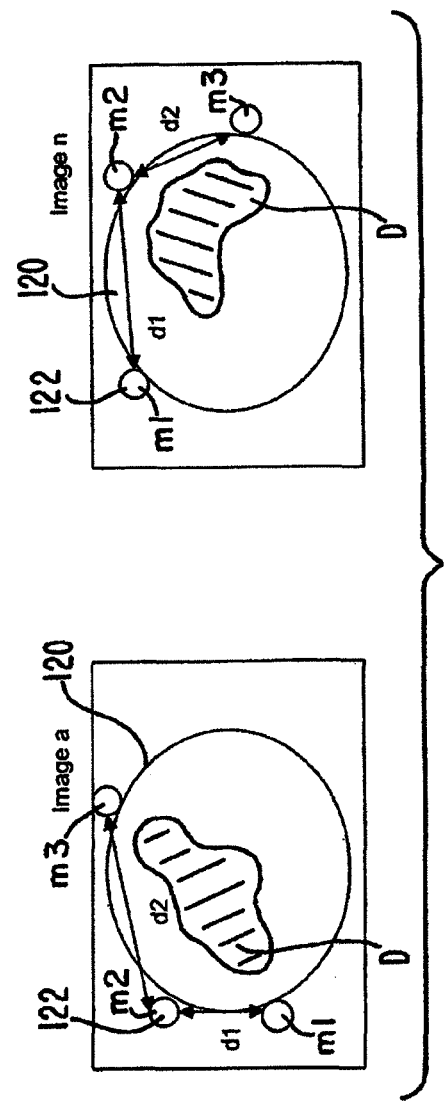
FIG. 4A
FIG. 4B

APPARATUS AND METHOD FOR FOUR DIMENSIONAL SOFT TISSUE NAVIGATION IN ENDOSCOPIC APPLICATIONS

CROSS-REFERENCE TO RELATED APPLICATIONS

This application claims the benefit of U.S. Provisional Application Ser. Nos. 61/375,439, filed Aug. 20, 2010, 61/375,484, filed Aug. 20, 2010, 61/375,523, filed Aug. 20, 2010, and 61/375,533, filed Aug. 20, 2010, each of which are hereby incorporated by reference in their entirety, including any figures, tables, and drawings.

BACKGROUND

The invention relates generally to a medical device and particularly to an apparatus and methods associated with a range of image guided medical procedures.

Image guided surgery (IGS), also known as image guided intervention (IGI), enhances a physician's ability to locate instruments within anatomy during a medical procedure. IGS can include 2-dimensional (2-D), 3-dimensional (3-D), and 4-dimensional (4-D) applications. The fourth dimension of IGS can include multiple parameters either individually or together such as time, motion, electrical signals, pressure, airflow, blood flow, respiration, heartbeat, and other patient measured parameters.

Existing imaging modalities can capture the movement of dynamic anatomy. Such modalities include electrocardiogram (ECG)-gated or respiratory-gated magnetic resonance imaging (MRI) devices, ECG-gated or respiratory-gated computer tomography (CT) devices, standard computed tomography (CT), 3D Fluoroscopic images (Angio-suites), and cinematography (CINE) fluoroscopy and ultrasound. Multiple image datasets can be acquired at different times, cycles of patient signals, or physical states of the patient. The dynamic imaging modalities can capture the movement of anatomy over a periodic cycle of that movement by sampling the anatomy at several instants during its characteristic movement and then creating a set of image frames or volumes.

A need exists for an apparatus that can be used with such imaging devices to capture pre-procedural or intra-procedural images of a targeted anatomical body and use those images intra-procedurally to help guide a physician to the correct location of the anatomical body during a medical procedure.

SUMMARY OF THE INVENTION

A method includes receiving during a first time interval image data associated with an image of a dynamic body. The image data includes an indication of a position of a first marker on a patient tracking device (PTD) coupled to the dynamic body and a position of a second marker on the PTD. Some registration methods such as 2D to 3D registration techniques allow for the image data containing the target or patient anatomy of interest to not contain the PTD. A registration step is performed to calculate the transformation from image space to patient space using an additional dataset to register (i.e., a 2D fluoroscopic set of images is used to register a 3D fluoroscopic dataset). This technique is not limited to fluoroscopic procedures as it can implemented in any procedure acquiring 2D images such as ultrasound, OCT (optical coherence tomography), EBUS (endobronchial ultrasound), or IVUS (intravascular ultrasound). This technique uses the markers that are within multiple 2D images to register the 3D volume that is reconstructed from these 2D images. The reconstructed 3D volume is smaller than the field of view of the 2D images, so this technique allows for the PTD markers to be visible in a subset of the 2D images, but not within the 3D volume. In certain embodiments, the first marker is coupled to the PTD at a first location and the second marker is coupled to the PTD at a second location. A distance between the position of the first marker and the position of the second marker is determined. During a second time interval after the first time interval, data associated with a position of a first localization element coupled to the PTD at the first location and data associated with a position of a second localization element coupled to the PTD at the second location are received. A distance between the first localization element and the second localization element based on the data associated with the position of the first localization element and the position of the second localization element is determined. A difference is calculated between the distance between the first marker and the second marker during the first time interval and the distance between the first localization element and the second localization element during the second time interval. In addition the PTD device can be tracked continuously during the procedure and a sequence of motion of the PTD device that represents the patient motion of an organ or the patient's respiratory cycle can be collected. The sequence of motion can then be analyzed to find unique similar points within the dataset and grouped.

Other objects and features will be in part apparent and in part pointed out hereinafter.

BRIEF DESCRIPTION OF THE DRAWINGS

The details of the present invention, both as to its construction and operation can best be understood with reference to the accompanying drawings, in which like numerals refer to like parts, and in which:

FIG. 4A is a schematic illustrating vector distances from a localization device according to an embodiment of the invention.

FIG. 4B is a schematic illustrating vector distances from image data according to an embodiment of the invention.

DETAILED DESCRIPTION

Figure 1:
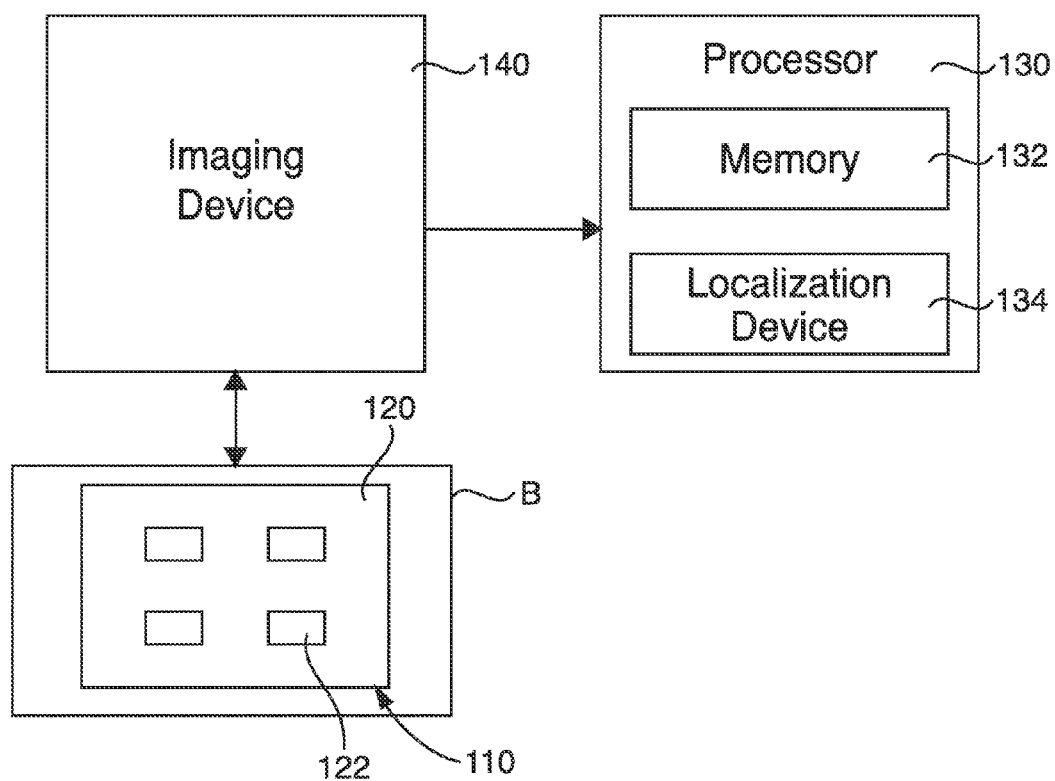
FIG. 1 is a schematic illustration of various devices used with a method according to an embodiment of the invention.

The accompanying Figures and this description depict and describe embodiments of a navigation system (and related methods and devices) in accordance with the present invention, and features and components thereof. It should also be noted that any references herein to front and back, right and left, top and bottom and upper and lower are intended for convenience of description, not to limit the present invention or its components to any one positional or spatial orientation.

It is noted that the terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. Thus, a method, an apparatus, or a system that "comprises," "has," "contains," or "includes" one or more items possesses at least those one or more items, but is not limited to possessing only those one or more items. For example, a method that comprises receiving a position of an instrument reference marker coupled to an instrument; transforming the position into image space using a position of a non-tissue internal reference marker implanted in a patient; and superimposing a representation of the instrument on an image in which the non-tissue internal reference marker appears possesses at least the receiving, transforming, and superimposing steps, but is not limited to possessing only those steps. Accordingly, the method also covers instances where the transforming includes transforming the position into image space using a transformation that is based, in part, on the position of the non-tissue internal reference marker implanted in the patient, and calculating the transformation using image space coordinates of the internal reference marker in the image. The term "use" should be interpreted the same way. Thus, a calculation that uses certain items uses at least those items, but also covers the use of additional items.

Individual elements or steps of the present methods, apparatuses, and systems are to be treated in the same manner. Thus, a step that calls for creating a dataset that includes images, one of the images (a) depicting a non-tissue internal reference marker, (b) being linked to non-tissue internal reference marker positional information, and (c) being at least 2-dimensional covers the creation of at least such a dataset, but also covers the creation of a dataset that includes images, where each image (a) depicts the non-tissue internal reference marker, and (b) is linked to non-tissue internal reference marker positional information.

The terms "a" and "an" are defined as one or more than one. The term "another" is defined as at least a second or more. The term "coupled" encompasses both direct and indirect connections, and is not limited to mechanical connections.

Those of skill in the art will appreciate that in the detailed description below, certain well known components and assembly techniques have been omitted so that the present methods, apparatuses, and systems are not obscured in unnecessary detail.

An apparatus according to an embodiment of the invention includes a PTD and two or more markers coupled to the PTD. The apparatus can also include two or more localization elements coupled to the PTD proximate the markers. The apparatus is configured to be coupled to a dynamic body, such as selected dynamic anatomy of a patient. Dynamic anatomy can be, for example, any anatomy that moves during its normal function (e.g., the heart, lungs, kidneys, liver and blood vessels). A processor, such as a computer, is configured to receive image data associated with the dynamic body taken during a pre-surgical or pre-procedural first time interval. The image data can include an indication of a position of each of the markers for multiple instants in time during the first time interval. The processor can also receive position data associated with the localization elements during a second time interval in which a surgical procedure or other medical procedure is being performed. The processor can use the position data received from the localization elements to determine a distance between the elements for a given instant in time during the second time interval. The processor can also use the image data to determine the distance between the markers for a given instant in time during the first time interval. The processor can then find a match between an image where the distance between the markers at a given instant in time during the first time interval is the same as the distance between the elements associated with those markers at a given instant in time during the medical procedure, or second time interval. Additionally, the processor can determine a sequence of motion of the markers and match this sequence of motion to the recorded motion of the markers over the complete procedure or significant period of time. Distance alone between the markers may not be sufficient to match the patient space to image space in many instances, it is important for the system to know the direction the markers are moving and the range and speed of this motion to find the appropriate sequence of motion for a complex signal or sequence of motion by the patient.

A physician or other healthcare professional can use the images selected by the processor during a medical procedure performed during the second time interval. For example, when a medical procedure is performed on a targeted anatomy of a patient, such as a heart or lung, the physician may not be able to utilize an imaging device during the medical procedure to guide him to the targeted area within the patient. A PTD according to an embodiment of the invention can be positioned or coupled to the patient proximate the targeted anatomy prior to the medical procedure, and pre-procedural images can be taken of the targeted area during a first time interval. Markers or fiducials coupled to the PTD can be viewed with the image data, which can include an indication of the position of the markers during a given path of motion of the targeted anatomy (e.g., the heart) during the first time interval. Such motion can be due, for example, to inspiration (i.e., inhaling) and expiration (i.e., exhaling) of the patient, or due to the heart beating. During a medical procedure, performed during a second time interval, such as a procedure on a heart or lung, the processor receives data from the localization elements associated with a position of the elements at a given instant in time during the medical procedure (or second time interval). The distance between selected pairs of markers can be determined from the image data and the distance, range, acceleration, and speed between corresponding selected pairs of localization elements can be determined based on the element data for given instants in time. From multiple image datasets the range and speed of the markers motion can be calculated.

Because the localization elements are coupled to the PTD proximate the location of the markers, the distance between a selected pair of elements can be used to determine an intra-procedural distance between the pair of corresponding markers to which the localization elements are coupled. An image from the pre-procedural image data taken during the first time interval can then be selected where the distance between the pair of selected markers in that image corresponds with or closely approximates the same distance determined using the localization elements at a given instant in time during the second time interval. This process can be done continuously during the medical procedure, producing simulated real-time, intra-procedural images illustrating the orientation and shape of the targeted anatomy as a catheter, sheath, needle, forceps, guidewire, fiducial delivery devices, therapy device (ablation modeling, drug diffusion modeling, etc.), or similar structure(s) is/are navigated to the targeted anatomy. Thus, during the medical procedure, the physician can view selected image(s) of the targeted anatomy that correspond to and simulate real-time movement of the anatomy. In addition, during a medical procedure being performed during the second time interval, such as navigating a catheter or other instrument or component thereof to a targeted anatomy, the location(s) of a sensor (e.g., an electromagnetic coil sensor) coupled to the catheter during the second time interval can be superimposed on an image of a catheter. The superimposed image(s) of the catheter can then be superimposed on the selected image(s) from the first time interval, providing simulated real-time images of the catheter location relative to the targeted anatomy. This process and other related methods are described U.S. Pat. No. 7,398,116, entitled Methods, Apparatuses, and Systems Useful in Conducting Image Guided Interventions, filed Aug. 26, 2003.

In one embodiment, a real-time pathway registration is applied to a pre-acquired dataset that does not contain the PTD. It will be understood that the pre-acquired dataset can be at only one cycle of a patient's respiratory, heartbeat, or other path of motion. In order to optimize the registration of a pre-acquired dataset that does not contain the PTD, a PTD can be subsequently applied to the patient, and the PTD signal can be used to collect registration information throughout full range or path of motion but only that information that is captured at a similar PTD orientation, shape, or point along the PTD cycle of motion is used. This method enhances the registration accuracy by ensuring that the registration points being used to register are at the same point during the initial dataset acquisition. In preferred embodiments, the method uses multiple subsets of the acquired registration data that are collected based on the PTD signal. These multiple subsets are then applied against the pre-acquired dataset to find the optimal registration fit.

In another embodiment, the device can be integrated with one or more fiber optic localization (FDL) devices and/or techniques. In this way, the sensor (such as an EM sensor) provides the 3D spatial orientation of the device, while the FDL provides shape sensing of the airway, vessel, pathway, organ, environment and surroundings. Conventional FDL techniques can be employed. In various embodiments, for example, the FDL device can be used to create localization information for the complete pathway or to refine the localization accuracy in a particular segment of the pathway. By either using 3D localization information, shape, or both detected by the FDL device, the system can use a weighted algorithm between multiple localization devices to determine the location and orientation of the instrument in the patient. The FDL device can also be used as or in conjunction with the PTD to track the patient's motion such as respiration or heartbeat.

Other aspects involve using a guidewire or other navigated instrument with one to one rotation to continuously align a virtual display view to be consistent with the actual bronchoscopic video view. A similar technique can be used with OCT, IVUS, or EBUS devices to orient the virtual view to the image captured by the OCT, IVUS, or EBUS devices.

Other aspects involve using video input of the bronchoscope to adjust the virtual "fly-through" view to be consistent with the user's normal perspective. For example, conventional video processing and matching techniques can be used to align the real-time video and the virtual image.

Other aspects involve using bronchoscopic video to provide angular information at a current location to provide targeting or directional cues to the user. Angular information can be derived from the location of patient anatomy in the image and the relative size of each within the image. Using information extracted from the video captured by the bronchoscope, the system can determine which the direction of the display. This can be done using, for example, translation, rotation, or a combination of both. Comparing the real-time image captured to the virtual image constructed from the 3D dataset (i.e., CT) the system can use this information to align the virtual image and/or enhance the system accuracy.

In another aspect, a high-speed three-dimensional imaging device, such as an optical coherence tomography (OCT) device, can be tracked. In accordance with conventional methods, such a device can only view 1-2 mm below the surface. With an EM sensor attached in accordance with the systems and methods described herein, multiple 3D volumes of data can be collected and a larger 3D volume of collected data can be constructed. Knowing the 3D location and orientation of the multiple 3D volumes will allow the user to view a more robust image of, for example, pre-cancerous changes in the esophagus or colon. This data can also be correlated to pre-acquired or intra-procedurally acquired CT, fluoroscopic, ultrasound, or 3D fluoroscopic images to provide additional information.

Among several potential enhancements that could be provided by an endolumenal system as described herein is that a user could overlay the planned pathway information on to the actual/real-time video image of the scope or imaging device (such as ultrasound based device). Additionally, the system and apparatus could provide a visual cue on the real-time video image showing the correct direction or pathway to take.

Additionally, or alternatively, one could use a 5DOF sensor and a limited or known range of motion of a localization device to determine its orientation in the field. This is particularly relevant, for example, in determining which way is up or down or the overall rotation of an image in 3D space. In bronchoscopy, for instance, this can be used to orient the bronchoscopic view to the user's normal expected visual orientation. Because a bronchoscope is typically only able to move in one plane up and down, the system can use the 3D location of a tip sensor moving up and down to determine the sixth degree of freedom. In this implementation, a user could steer the bronchoscope to a bifurcation or close to a bifurcation and then perform a motion with the scope (e.g., up and down) using the thumb control to wiggle or flutter the tip and sensor. With this motion (i.e., described herein generally as the "wiggle maneuver"), the system can determine the orientation and display the correct image. Typically, 5DOF sensing of instrument tip POSE (position and orientation) determines 5 of the 6 POSE parameters (x, y, z, pitch, and yaw). Such sensing may be unable in certain applications, however, to determine the instantaneous roll of the device. This roll determination can be critical in matching the video coming from the device to the images. The techniques described herein advantageously allow for users to relate orientation of a virtual endoscopic "fly-thru" display to actual video orientation presented by the endoscopic instrument.

Figure 20:
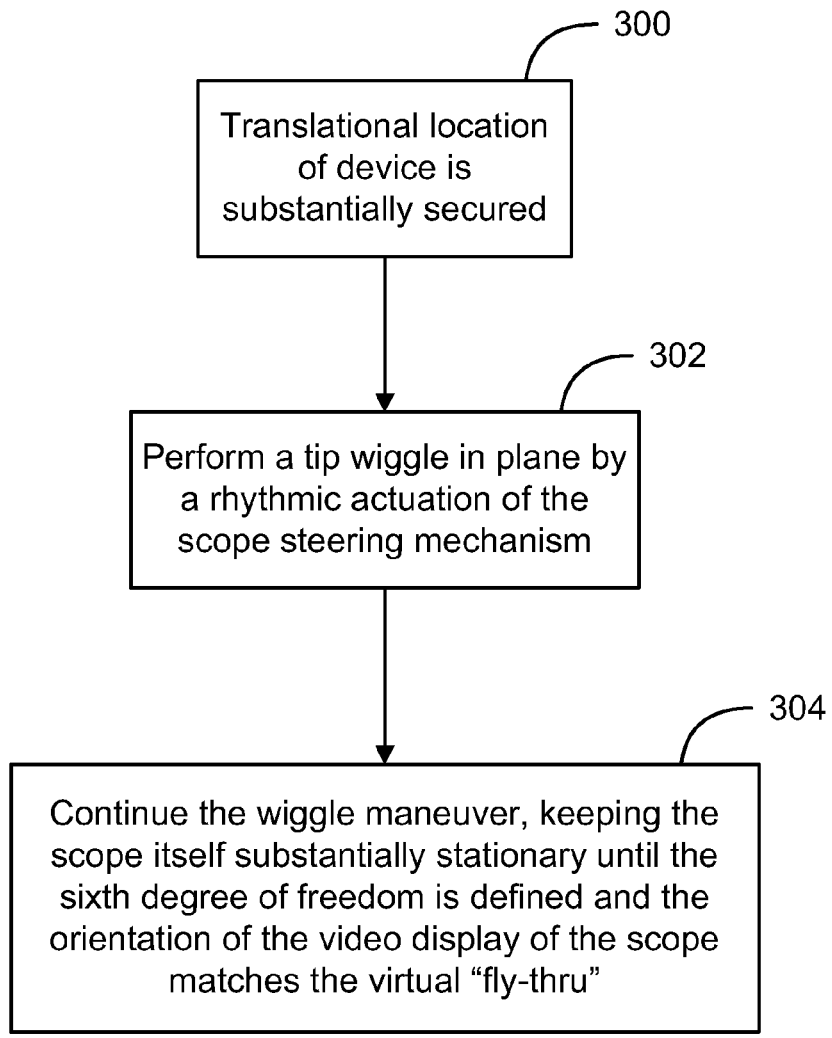
FIG. 20 is a flowchart that depicts a "wiggle maneuver" for defining the sixth degree of freedom of a 5DOF sensor in accordance with the invention described herein.

In general, the methods described herein provides for the user to select a location, most typically at a branching point in the bronchial tree, and perform a "wiggle" maneuver with the tip of the device. In preferred embodiments, as illustrated in FIG. 20, the wiggle maneuver generally consists of three steps:

(i). At step 300, at desired branch or other point, the physical or translational location of device is substantially secured or held in place. For example, with a bronchoscope, the user should ensure that the scope is held securely so it cannot translate relative to the airway.

(ii). At step 302, perform a tip wiggle in plane by a rhythmic actuation of the scope steering mechanism. The magnitude of the actuation should be sufficient in force for the tip to cover an approximate 1 cm-2 cm range of motion, but less motion may be sufficient in some applications or embodiments.

(iii). At step 304, continue the wiggle maneuver, keeping the scope itself substantially stationary until the systems described herein and related software defines the sixth degree of freedom, and the orientation of the video display of scope matches the virtual "fly-thru".

Algorithmically, a manifestation of an algorithm to detect this operation consists of recognizing a unique signature of motion over time. One such technique, for example, consists of two parts:

(a) performance of a continuous PCA analysis of a specified time window of 5DOF sensor locations. A repeated motion in a plane by the instrument tip will produce a covariance matrix such that the foremost eigenvalue (e0) will reflect the variance of a 1 cm-2 cm motion over a given time window. In addition, the secondary and tertiary eigenvalues (e1 and e2) will reflect a very small variance, as the tip should preferably be moving in an arc constrained to the plane defined by the spline mechanism of the scope.

(b) once an appropriate PCA signature is detected, orientation of the tip to the eigenvector E0, which represents the historical vector of motion for the instrument tip, is compared. An exemplary way to do this is the dot product of the measured tip vector and E0, which represents the acute angle.

$$r = V \cdot E0$$

By way of example and not by way of limitation, in an ideal wiggle maneuver, the orientation of the tip should show a rhythmic oscillation of about 90° (approximate range could be for instance +/−45°). This comparison of tip orientation to E0 provides the basis for a determination of the wiggle plane normal using, for example, a cross-product or gram-schmidt orthogonalization. The physical wiggle plane normal is in a constant relationship to the coordinate space of the video signal, and thus can be related (calibrated) thereto.

Interestingly, this algorithm can be used in a variety of different modes to detect certain forms of scope motion:

stationary scope (wherein the e0, e1, and e2 values will be very small and roughly equal, representing the small magnitude, unbiased Gaussian noise of the direct localization measurement);

scope in motion along a straight line in space, such as when traversing individual segments (wherein the e0 will be very large, with very small e1 and e2 values, representing a large co-linear translation in space). In addition, the absolute value of r will be close to 1, indicating that the orientation of the tip is nearly collinear with the translation of the tip over time.

In general, the wiggle techniques described herein for determining direction and orientation, including "up" and "down" orientation relative to (or independent of) the instrument steering mechanism, may used in a range of different endoscopic applications. Although the above examples and embodiments generally refer to the use of the wiggle maneuver in connection with bronchoscopic applications, it will be understood that the techniques described herein may also be used in other applications including, but not limited to, enteroscopy, colonoscopy, sigmoidoscopy, rhinoscopy, proctoscopy, otoscopy, cystoscopy, gynoscopy, colposcopy, hysteroscopy, falloposcopy, laparoscopy, arthroscopy, thoracoscopy, amnioscopy, fetoscopy, panendoscopy, epiduroscopy, and the like. The wiggle techniques described herein may also be applicable in non-medical endoscopic uses, such as the internal inspection of complex technical systems, surveillance, and the like.

In general, the systems and methods described herein can be implemented regardless of the number of sensors that are used. In some embodiments, serial orientation or positioning of multiple sensors allows the determination of one or more parameters such as shape, position, orientation, and mechanical status of a complete or partial section of guidewire or other device or instrument. For example, the placement of multiple sensors can assist in visualizing the shape of the device and any bends in the path by providing a number of data points on the path (e.g., 8 sensors, spaced 1 mm apart) to create a 3D shape model of the device. Various parameters can be used to track past or present movement and changes in device shape including, for example, elasticity, bend radius, limiting, and durometer rating of the device material. These parameters and accompanying data can provide visual cues to the user during the procedure, for example, when the device has a certain bend or curvature (based on path or surroundings), e.g., to provide a notice or warning that the device is on the correct or incorrect path, or to provide notice regarding, or track, a particular parameter(s) that the user is interested in.

Figure 18:
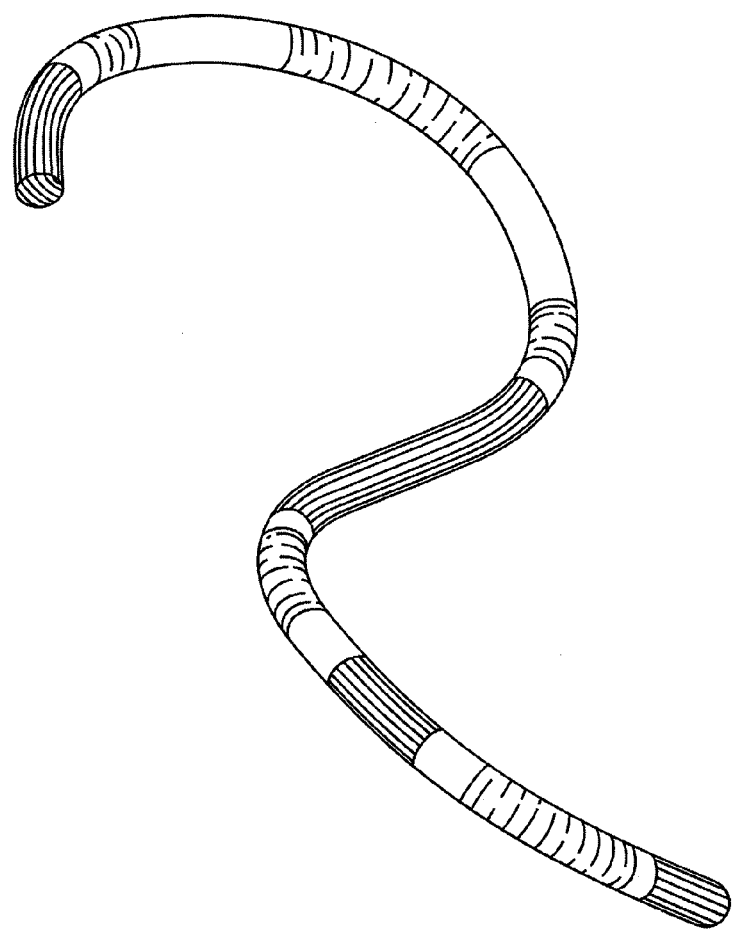
FIG. 18 depicts an exemplary curvature warning system in accordance with the invention described herein.

Such a sensor pathway is generally depicted in FIG. 18, which shows exemplary curvature warning scenarios in the differently marked sections or segments.

In various aspects and embodiments described herein, one can use the knowledge of the path traveled by the instrument and segmented airway or vessel from the acquired image (e.g., CT) to limit the possibilities of where the instrument is located in the patient. The techniques described herein, therefore, can be valuable to improve virtual displays for users. Fly through, Fly-above, or image displays related to segmented paths are commonly dependent upon relative closeness to the segmented path. For a breathing patient, for example, or a patient with a moving vessel related to heartbeat, it is valuable to use the path traveled information to determine where in the 4D patient motion cycle the system is located within the patient. By comparing the 3D location, the patient's tracked or physiological signal is used to determine 4D patient motion cycle, and with the instrument's traveled path, one can determine the optical location relative to a segmented airway or vessel and use this information to provide the optimal virtual display.

Figure 2:
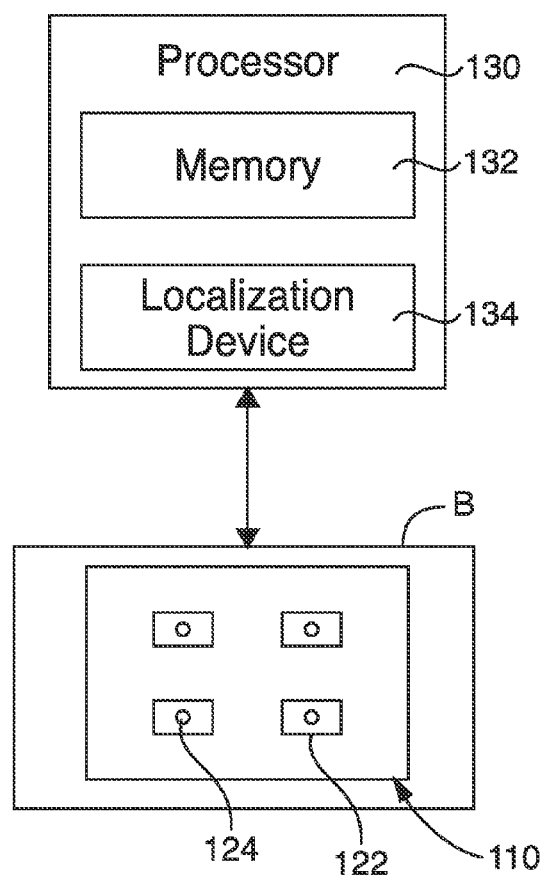
FIG. 2 is a schematic illustration of various devices used with a method according to an embodiment of the invention.

FIGS. 1 and 2 are schematic illustrations of devices that can be used in conjunction with, or to perform, various procedures described herein. As shown in FIG. 1, an apparatus 110 includes a PTD 120. The PTD 120 can be coupled to a dynamic body B. The dynamic body B can be, for example, a selected dynamic portion of the anatomy of a patient. The PTD 120 can be a variety of different shapes and sizes. For example, in one embodiment the PTD 120 is substantially planar, such as in the form of a patch that can be disposed at a variety of locations on a patient's body. Such a PTD 120 can be coupled to the dynamic body with adhesive, straps, hook and pile, snaps, or any other suitable coupling method. In another embodiment the PTD can be a catheter type device with a pigtail or anchoring mechanism that allows it to be attached to an internal organ or along a vessel.

Two or more markers or fiducials 122 are coupled to the PTD 120 at selected locations as shown in FIG. 1. The markers 122 are constructed of a material that can be viewed on an image, such as an X-ray or CT. The markers 122 can be, for example, radiopaque, and can be coupled to the PTD 120 using any known methods of coupling such devices. FIGS. 1 and 2 illustrate the apparatus 110 having four markers 122, but any number of two or more markers can be used. In one embodiment the marker or fiducials and the localization element can be the same device.

An imaging device 140 can be used to take images of the dynamic body B while the PTD 120 is coupled to the dynamic body B, pre-procedurally during a first time interval. As stated above, the markers 122 are visible on the images and can provide an indication of a position of each of the markers 122 during the first time interval. The position of the markers 122 at given instants in time through a path of motion of the dynamic body B can be illustrated with the images. The imaging device 140 can be, for example, a computed tomography (CT) device (e.g., respiratory-gated CT device, ECG-gated CT device), a magnetic resonance imaging (MRI) device (e.g., respiratory-gated MRI device, ECG-gated MRI device), an X-ray device, or any other suitable medical imaging device. In one embodiment, the imaging device 140 is a computed tomography—positron emission tomography device that produces a fused computed tomography—positron emission tomography image dataset. The imaging device 140 can be in communication with a processor 130 and send, transfer, copy and/or provide image data taken during the first time interval associated with the dynamic body B to the processor 130.

The processor 130 includes a processor-readable medium storing code representing instructions to cause the processor 130 to perform a process. The processor 130 can be, for example, a commercially available personal computer, or a less complex computing or processing device that is dedicated to performing one or more specific tasks. For example, the processor 130 can be a terminal dedicated to providing an interactive graphical user interface (GUI). The processor 130, according to one or more embodiments of the invention, can be a commercially available microprocessor. Alternatively, the processor 130 can be an application-specific integrated circuit (ASIC) or a combination of ASICs, which are designed to achieve one or more specific functions, or enable one or more specific devices or applications. In yet another embodiment, the processor 130 can be an analog or digital circuit, or a combination of multiple circuits.

The processor 130 can include a memory component 132. The memory component 132 can include one or more types of memory. For example, the memory component 132 can include a read only memory (ROM) component and a random access memory (RAM) component. The memory component can also include other types of memory that are suitable for storing data in a form retrievable by the processor 130. For example, electronically programmable read only memory (EPROM), erasable electronically programmable read only memory (EEPROM), flash memory, as well as other suitable forms of memory can be included within the memory component. The processor 130 can also include a variety of other components, such as for example, coprocessors, graphic processors, etc., depending upon the desired functionality of the code.

The processor 130 can store data in the memory component 132 or retrieve data previously stored in the memory component 132. The components of the processor 130 can communicate with devices external to the processor 130 by way of an input/output (I/O) component (not shown). According to one or more embodiments of the invention, the I/O component can include a variety of suitable communication interfaces. For example, the I/O component can include, for example, wired connections, such as standard serial ports, parallel ports, universal serial bus (USB) ports, S-video ports, local area network (LAN) ports, small computer system interface (SCCI) ports, and so forth. Additionally, the I/O component can include, for example, wireless connections, such as infrared ports, optical ports, Bluetooth® wireless ports, wireless LAN ports, or the like.

The processor 130 can be connected to a network, which may be any form of interconnecting network including an intranet, such as a local or wide area network, or an extranet, such as the World Wide Web or the Internet. The network can be physically implemented on a wireless or wired network, on leased or dedicated lines, including a virtual private network (VPN).

As stated above, the processor 130 can receive image data from the imaging device 140. The processor 130 can identify the position of selected markers 122 within the image data or voxel space using various segmentation techniques, such as Hounsfield unit thresholding, convolution, connected component, or other combinatory image processing and segmentation techniques. The processor 130 can determine a distance and direction between the position of any two markers 122 during multiple instants in time during the first time interval, and store the image data, as well as the position and distance data, within the memory component 132. Multiple images can be produced providing a visual image at multiple instants in time through the path of motion of the dynamic body. The processor 130 can also include a receiving device or localization device 134, which is described in more detail below.

A deformation field may also be included in the analysis in various embodiments described herein. For example, the deformation field can be applied to fuse 3D fluoroscopic images to CT images in order to compensate for different patient orientations, patient position, respiration, deformation induced by the catheter or other instrument, and/or other changes or perturbations that occur due to therapy delivery or resection or ablation of tissue.

In some embodiments, for example, real-time respiration compensation can be determined by applying an inspiration-to-expiration deformation vector field. In combination with the PTD respiratory signal, for example, the instrument location can be calculated using the deformation vector field. A real-time instrument tip correction vector can be applied to a 3D localized instrument tip. The real-time correction vector is computed by scaling an inspiration-to-expiration deformation vector (found from the inspiration-to-expiration deformation vector field) based on the PTD respiratory signal. This correction vector can then be applied to the 3D localized instrument tip. This can further optimize accuracy during navigation.

Figure 19:
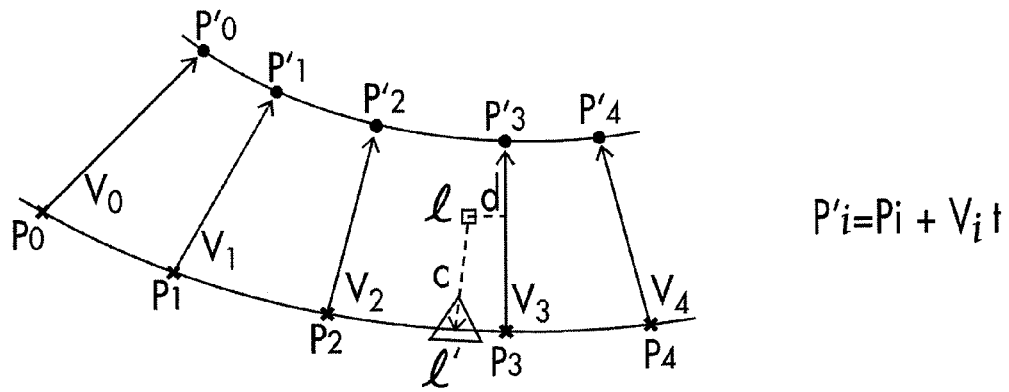
FIG. 19 depicts an exemplary real-time respiration compensation algorithm.

An example of an algorithm for real-time respiration compensation can be found in FIG. 19. In accordance with this algorithm, for each l:
(a) find $v_t$ such that scalar d is minimized;
(b) compute c, wherein:

$$c = -v_t t$$

and (c) compute l', wherein:

$$l' = l_{+c}$$

Thus, l' is a respiration compensated version of l.

Although FIG. 19 and the above discussion generally relate to real-time respiration motion, it will be understood that these calculations and determinations may also be applied to real-time heartbeat and/or vessel motion compensation, or any other motion of a dynamic body as described herein. In one embodiment, for example, the deformation matrix is calculated based upon inspiration and expiration. In another embodiment, for example, the deformation matrix is calculated based upon heartbeat. In yet another embodiment, for example, the deformation matrix is based upon vessel motion. In these and other embodiments, it is also possible to extend these calculations and determinations to develop multiple deformation matrices across multiple patient datasets, by acquiring the multiple datasets over the course of, for example, a single heartbeat cycle or a single respiratory cycle.

Deformation on 2D images can also be calculated based upon therapeutic change of tissue, changes in Houndsfield units for images, patient motion compensation during the imaging sequence, therapy monitoring, and temperature monitoring with fluoroscopic imaging, among other things. One potential issue with conventional therapy delivery, for instance, is monitoring the therapy for temperature or tissue changes. In accordance with the methods described herein, this monitoring can be carried out using intermittent fluoroscopic imaging, where the images are compensated between acquisition times to show very small changes in image density, which can represent temperature changes or tissue changes as a result of the therapy and/or navigation.

In general, it may also be preferable to reduce the level of radiation that patients are exposed to before or during a procedure (or pre-procedural analysis) as described herein. One method of reducing radiation during the acquisition of a 3D fluoroscopic dataset (or other dataset described herein), for example, is to use a deformation field between acquired 2D images to reduce the actual number of 2D images that need to be acquired to create the 3D dataset. In one particular embodiment, the deformation field is used to calculate the deformation between images in the acquisition sequence to produce 2D images between the acquired slices, and these new slices can be used to calculate the 3D fluoroscopic dataset. For example, if 180 2D image slices were previously required, e.g., an image(s) taken every 2 degrees of a 360 degree acquisition sequence, in accordance with some embodiments 90 2D images can be acquired over a 360 degree acquisition sequence and the data from the images that would have ordinarily been acquired between each slice can be calculated and imported into the 3D reconstruction algorithm. Thus, the radiation is effectively reduced by 50%.

As shown in FIG. 2, two or more localization elements 124 are coupled to the PTD 120 proximate the locations of the markers 122 for use during a medical procedure to be performed during a second time interval. The localization elements 124 can be, for example, electromagnetic coils, infrared light emitting diodes, and/or optical passive reflective markers. The localization elements 124 can also be, or be integrated with, one or more fiber optic localization (FDL) devices. The markers 122 can include plastic or non-ferrous fixtures or dovetails or other suitable connectors used to couple the localization elements 124 to the markers 122. A medical procedure can then be performed with the PTD 120 coupled to the dynamic body B at the same location as during the first time interval when the pre-procedural images were taken. During the medical procedure, the localization elements 124 are in communication or coupled to the localization device 134 included within processor 130. The localization device 134 can be, for example, an analog to digital converter that measures voltages induced onto localization coils in the field; creates a digital voltage reading; and maps that voltage reading to a metric positional measurement based on a characterized volume of voltages to millimeters from a fixed field emitter. Position data associated with the elements 124 can be transmitted or sent to the localization device 134 continuously during the medical procedure during the second time interval. Thus, the position of the localization elements 124 can be captured at given instants in time during the second time interval. Because the localization elements 124 are coupled to the PTD 120 proximate the markers 122, the localization device 134 can use the position data of the elements 124 to deduce coordinates or positions associated with the markers 122 intra-procedurally during the second time interval. The distance, range, acceleration, and speed between one or more selected pairs of localization elements 124 (and corresponding markers 122) can then be determined and various algorithms can be used to analyze and compare the distance between selected elements 124 at given instants in time, to the distances between and orientation among corresponding markers 122 observed in the pre-operative images.

An image can then be selected from the pre-operative images taken during the first time interval that indicates a distance or is grouped in a similar sequence of motion between corresponding markers 122 at a given instant in time, that most closely approximates or matches the distance or similar sequence of motion between the selected elements 124. The process of comparing the distances is described in more detail below. Thus, the apparatus 110 and processor 130 can be used to provide images corresponding to the actual movement of the targeted anatomy during the medical procedure being performed during the second time interval. The images illustrate the orientation and shape of the targeted anatomy during a path of motion of the anatomy, for example, during inhaling and exhaling.

Figure 3:
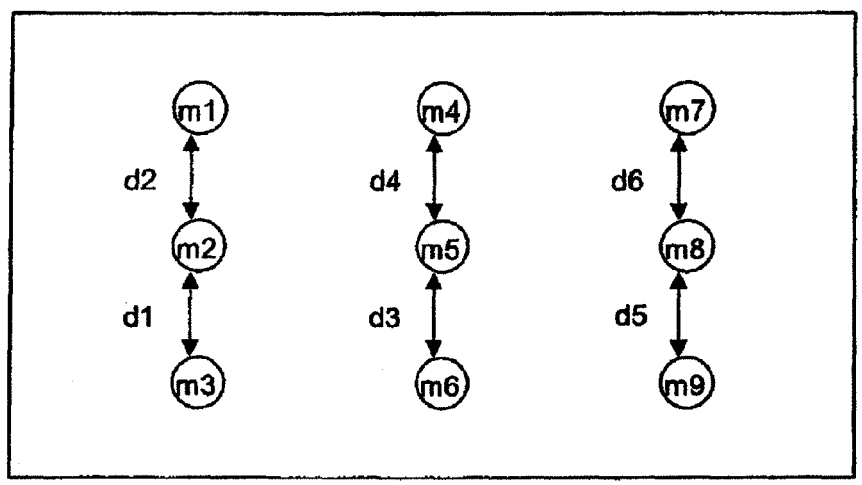
FIG. 3 is a schematic illustrating vector distances on an apparatus according to an embodiment of the invention.

FIG. 3 illustrates an example set of distances or vectors d1 through d6 between a set of markers 122, labeled m1 through m9 that are disposed at spaced locations on a PTD 120. As described above, pre-procedure images can be taken of a dynamic body for which the PTD 120 is to be coupled during a first time interval. The distances between the markers can be determined for multiple instants in time through the path of motion of the dynamic body. Then, during a medical procedure, performed during a second time interval, localization elements (not shown in FIG. 3) coupled proximate to the location of markers 122 can provide position data for the elements to a localization device (not shown in FIG. 3). The localization device can use the position data to determine distances or vectors between the elements for multiple instants in time during the medical procedure or second time interval.

FIG. 4A shows an example of distance or vector data from the localization device. Vectors a1 through a6 represent distance data for one instant in time and vectors n1 through n6 for another instant in time, during a time interval from a to n. As previously described, the vector data can be used to select an image from the pre-procedural images that includes distances between the markers m1 through m9 that correspond to or closely approximate the distances a1 through a6 for time a, for example, between the localization elements. The same process can be performed for the vectors n1 through n6 captured during time n.

One method of selecting the appropriate image from the pre-procedural images is to execute an algorithm that can sum all of the distances a1 through a6 and then search for and match this sum to an image containing a sum of all of the distances d1 through d6 obtained pre-procedurally from the image data that is equal to the sum of the distances a1 through a6. When the difference between these sums is equal to zero, the relative position and orientation of the anatomy or dynamic body D during the medical procedure will substantially match the position and orientation of the anatomy in the particular image. The image associated with distances d1 through d6 that match or closely approximate the distances a1 through a6 can then be selected and displayed. For example, FIG. 4B illustrates examples of pre-procedural images, Image a and Image n, of a dynamic body D that correspond to the distances a1 through a6 and n1 through n6, respectively. An example of an algorithm for determining a match is as follows:

Does $\Sigma a_i = \Sigma d_i$ ($i=1$ to 6 in this example) OR

Does $\Sigma (a_i - d_i) = 0$ ($i=1$ to 6 in this example).

If yes to either of these, then the image is a match to the vector or distance data obtained during the medical procedure.

Figure 5:
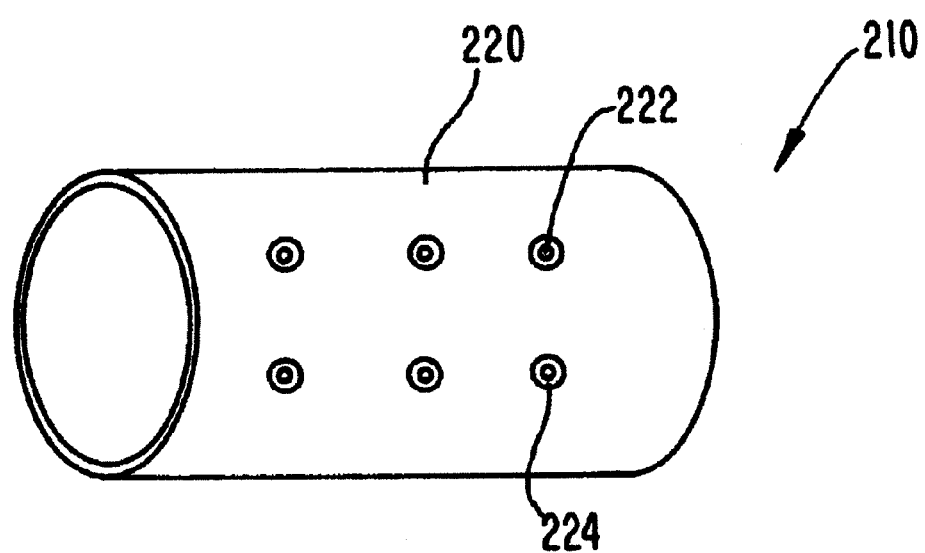
FIG. 5 is a front perspective view of an apparatus according to an embodiment of the invention.

FIG. 5 illustrates an apparatus 210 according to an embodiment of the invention. The apparatus 210 includes a tubular shaped PTD 220 that can be constructed with a rigid material or, alternatively, a flexible and/or stretchable material. In one embodiment, for example, the PTD 220 is substantially rigid in structure. In another embodiment, for example, the PTD 220 has a flexible or stretchable structure. The PTD 220 can be positioned over a portion of a patient's body, such as around the upper or lower torso of the patient. In the embodiments in which the PTD 220 is constructed with a stretchable and/or flexible material, for instance, the stretchability of the PTD 220 allows the PTD 220 to at least partially constrict some of the movement of the portion of the body for which it is coupled. The apparatus 210 further includes multiple markers or fiducials 222 coupled to the PTD 220 at spaced locations. A plurality of localization elements 224 are removably coupled proximate to the locations of markers 222, such that during a first time interval as described above, images can be taken without the elements 224 being coupled to the PTD 220. The localization elements need not be removably coupled. For example, the elements can be fixedly coupled to the PTD. In addition, the elements can be coupled to the PTD during the pre-procedure imaging.

Figure 6:
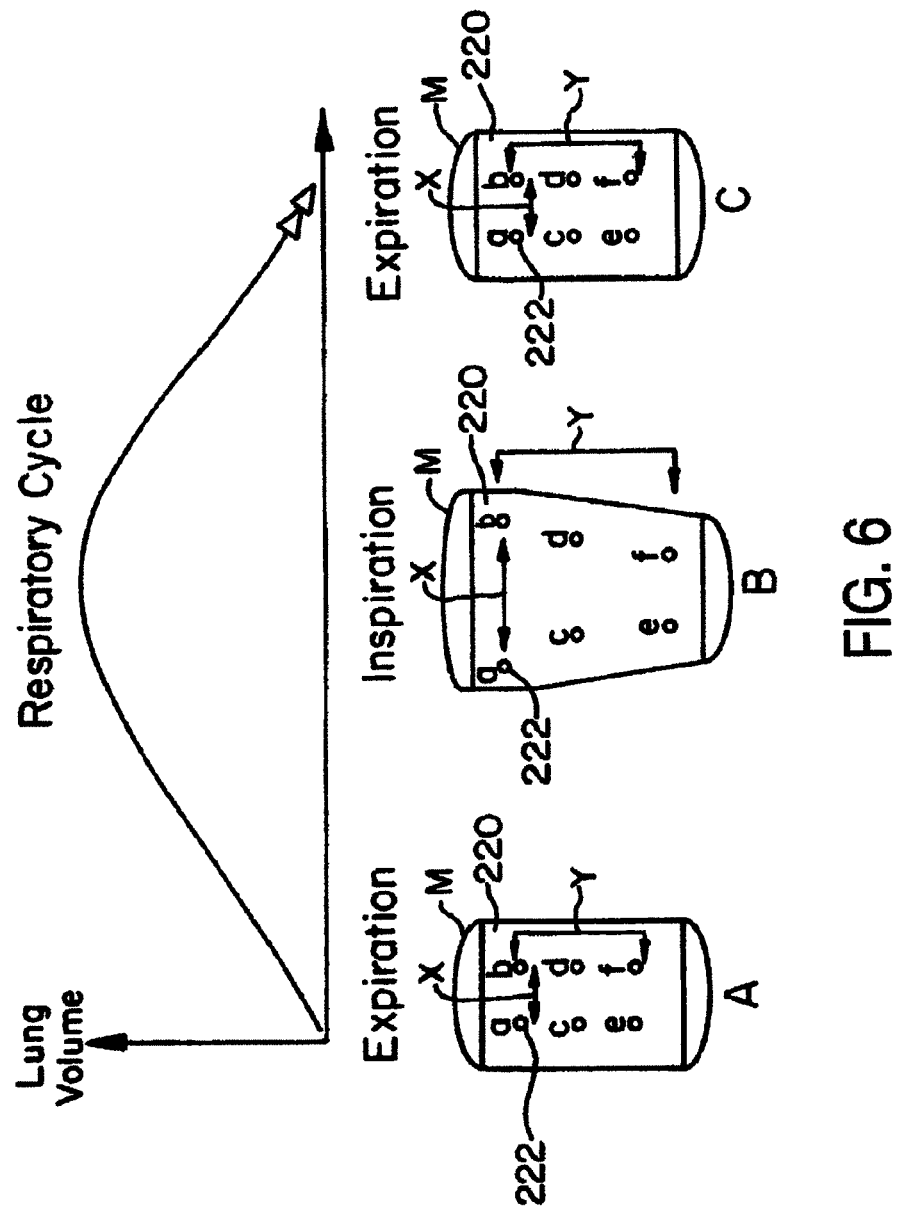
FIG. 6 is a graphical representation illustrating the function of an apparatus according to an embodiment of the invention.

FIG. 6 is a graphical illustration indicating how the apparatus 210 (shown without localization elements 224) can move and change orientation and shape during movement of a dynamic body, such as a mammalian body M. The graph is one example of how the lung volume can change during inhalation (inspiration) and exhalation (expiration) of the mammalian body M. The corresponding changes in shape and orientation of the apparatus 210 during inhalation and exhalation are also illustrated. The six markers 222 shown in FIG. 5 are labeled a, b, c, d, e, and f. As described above, images of the apparatus 210 can be taken during a first time interval. The images can include an indication of relative position of each of the markers 222, that is the markers 222 are visible in the images, and the position of each marker 222 can then be observed over a period of time. A distance between any two markers 222 can then be determined for any given instant of time during the first time interval. For example, a distance X between markers a and b is illustrated, and a distance Y between markers b and f is illustrated. These distances can be determined for any given instant in time during the first time interval from an associated image that illustrates the position and orientation of the markers 222. As illustrated, during expiration of the mammalian body M at times indicated as A and C, the distance X is smaller than during inspiration of the mammalian body M, at the time indicated as B. Likewise, the distance Y is greater during inspiration than during expiration. The distance between any pair of markers 222 can be determined and used in the processes described herein. Thus, the above embodiments are merely examples of possible pair selections. For example, a distance between a position of marker e and a position of marker b may be determined. In addition, multiple pairs or only one pair may be selected for a given procedure.

Figure 7:
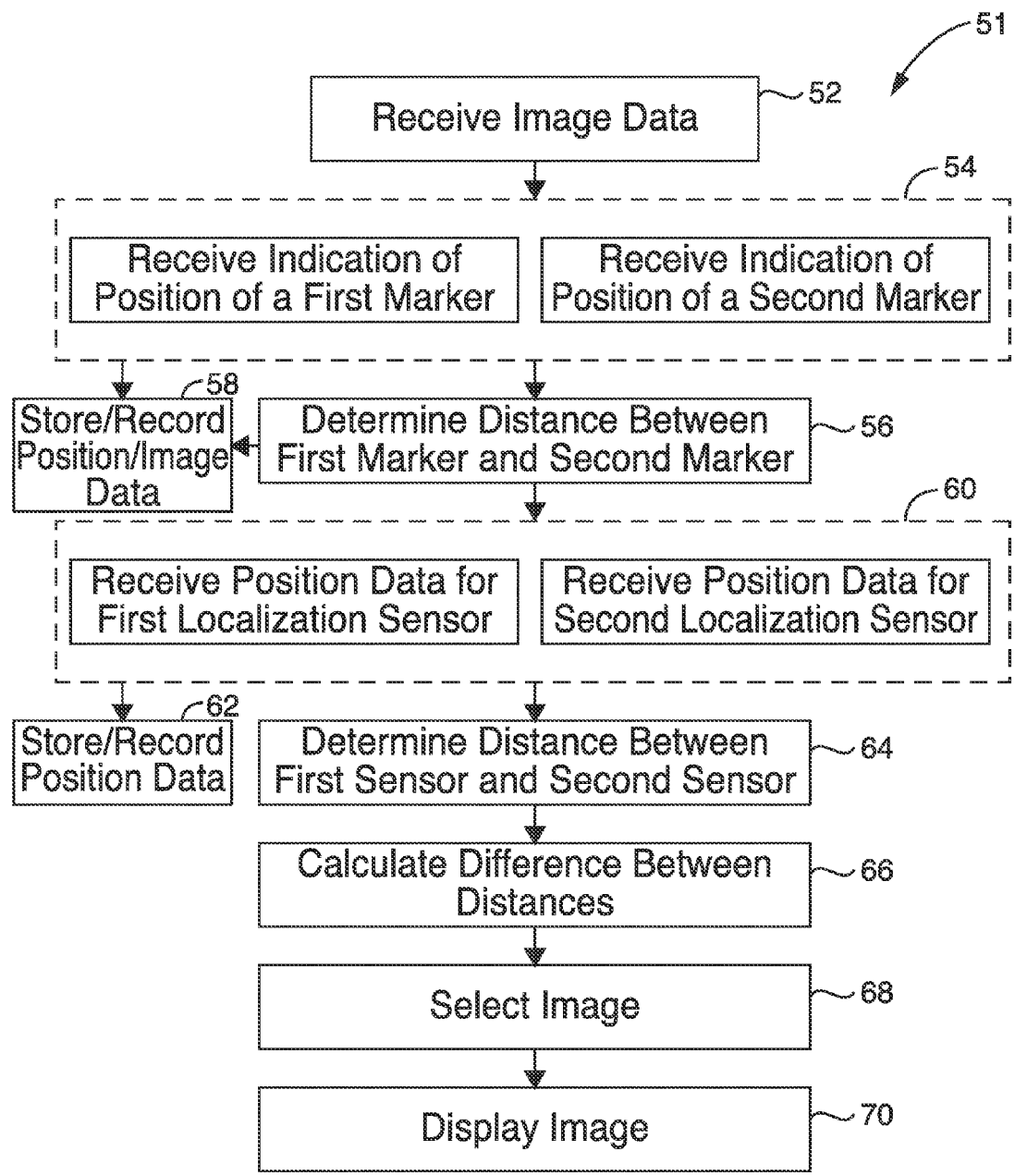
FIG. 7 is a flowchart illustrating a method according to an embodiment of the invention.

FIG. 7 is a flowchart illustrating a method according to an embodiment of the invention. A method 51 includes at step 52 receiving image data during a pre-procedural or first time interval. As discussed above, images are taken of a dynamic body using an appropriate imaging modality (e.g., CT Scan, MRI, etc.). The image data is associated with one or more images taken of a PTD (as described herein) coupled to a dynamic body, where the PTD includes two or more markers coupled thereto. In other words, the image data of the dynamic body is correlated with image data related to the PTD. The one or more images can be taken using a variety of different imaging modalities as described previously. The image data can include an indication of a position of a first marker and an indication of a position of a second marker, as illustrated at step 54. The image data can include position data for multiple positions of the markers during a range or path of motion of the dynamic body over a selected time interval. As described above, the image data can include position data associated with multiple markers, however, only two are described here for simplicity. A distance between the position of the first marker and the position of the second marker can be determined for multiple instants in time during the first time interval, at step 56. As also described above, the determination can include determining the distance based on the observable distance between the markers on a given image. The image data, including all of the images received during the first time interval, the position, and the distance data can be stored in a memory and/or recorded at step 58.

Then at step 60, during a second time interval, while performing a medical procedure on the patient with the PTD positioned on the patient at substantially the same location, position data can be received for a first localization element and a second localization element. The localization elements can be coupled to the PTD proximate the locations of the markers, such that the position data associated with the elements can be used to determine the relative position of the markers in real-time during the medical procedure. The position data of the elements can be stored and/or recorded at step 62.

A distance between the first and second localization elements can be determined at step 64. Although only two localization elements are described, as with the markers, position data associated with more than two localization elements can be received and the distances between the additional elements can be determined.

The next step is to determine which image from the one or more images taken during the first time interval represents the relative position and/or orientation of the dynamic body at a given instant in time during the second time interval or during the medical procedure. To determine this, at step 66, the distance between the positions of the first and second localization elements at a given instant in time during the second time interval are compared to the distance(s) determined in step 56 between the positions of the first and second markers obtained with the image data during the first time interval.

An image can be selected from the first time interval that best represents the same position and orientation of the dynamic body at a given instant in time during the medical procedure. To do this, the difference between the distance between a given pair of localization elements during the second time interval is used to select the image that contains the same distance between the same given pair of markers from the image data received during the first time interval. This can be accomplished, for example, by executing an algorithm to perform the calculations. When there are multiple pairs of markers and localization elements, the algorithm can sum the distances between all of the selected pairs of elements for a given instant in time during the second time interval and sum the distances between all of the associated selected pairs of markers for each instant in time during the first time interval when the pre-procedural image data was received.

When an image is found that provides the sum of distances for the selected pairs of markers that is substantially the same as the sum of the distances between the localization elements during the second time interval, then that image is selected at step 68. The selected image can then be displayed at step 70. The physician can then observe the image during the medical procedure on a targeted portion of the dynamic body. Thus, during the medical procedure, the above process can be continuously executed such that multiple images are displayed and images corresponding to real-time positions of the dynamic body can be viewed.

Figure 8:
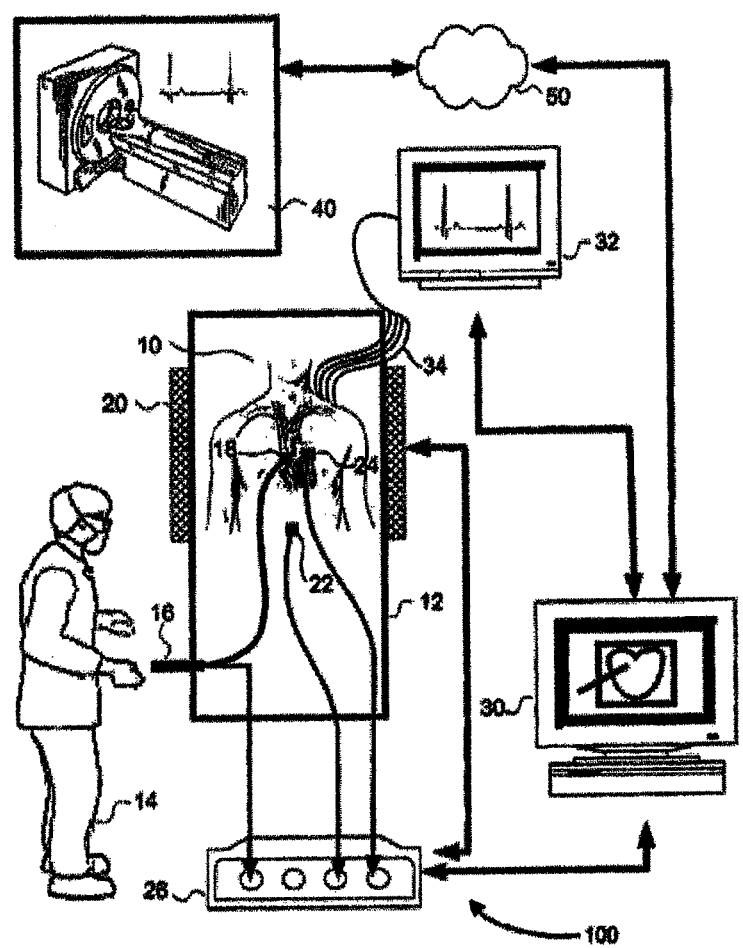
FIG. 8 shows the layout of a system that may be used to carry out image guided interventions using certain of the present methods that involve gated datasets.

FIG. 8 shows one embodiment of a system (system 100) that includes components that can be used to perform image guided interventions using a gated imaging modality, such as ECG-gated MRI, or ECG-gated CT. The figure depicts a patient 10 positioned on an operating table 12 with a physician 14 performing a medical procedure on him.

Specifically, FIG. 8 depicts physician 14 steering a medical instrument 16 through the patient's internal anatomy in order to deliver therapy. In this particular instance, instrument 16 is depicted as a catheter entering the right atrium by way of the inferior vena cava preceded by a femoral artery access point; however, the present systems are not limited to catheter use indications. The position of virtually any instrument may be tracked as discussed below and a representation of it superimposed on the proper image, consistent with the present methods, apparatuses, and systems. An "instrument" is any device controlled by physician 14 for the purpose of delivering therapy, and includes needles, guidewires, stents, filters, occluders, retrieval devices, imaging devices (such as OCT, EBUS, IVUS, and the like), and leads. Instrument 16 is fitted with one or more instrument reference markers 18. A tracker 20 (which is sometimes referred to in the art as a "tracking system") is configured to track the type of reference marker or markers coupled to instrument 16. Tracker 20 can be any type of tracking system, including but not limited to an electromagnetic tracking system. An example of a suitable electromagnetic tracking system is the AURORA electromagnetic tracking system, commercially available from Northern Digital Inc. in Waterloo, Ontario Canada. If tracker 20 is an electromagnetic tracking system, element 20 would represent an electromagnetic field generator that emits a series of electromagnetic fields designed to engulf patient 10, and reference marker or markers 18 coupled to medical instrument 16 could be coils that would receive an induced voltage that could be monitored and translated into a coordinate position of the marker(s).

Figure 21A:
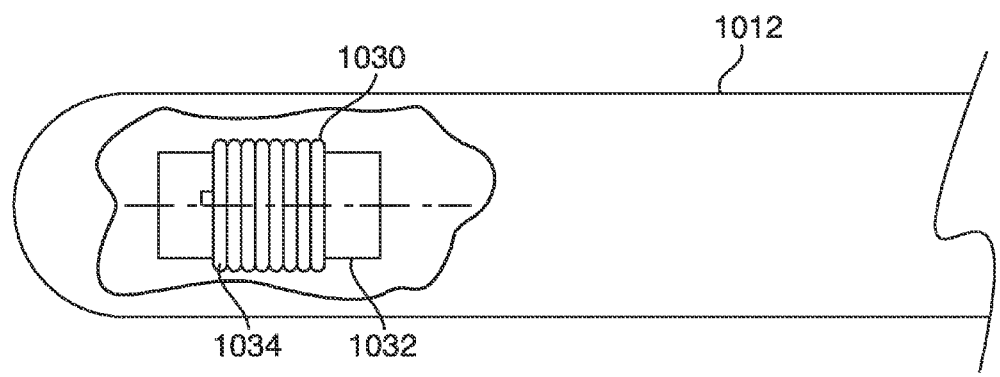
FIG. 21A is a front view of a tip sensor in a surgical instrument in accordance with the invention described herein.
Figure 21B:
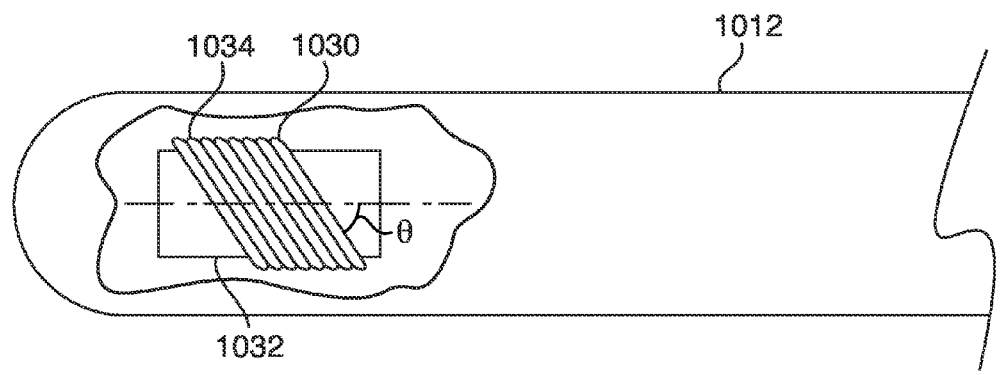
FIG. 21B is a front view of a tip sensor in a surgical instrument in accordance with the invention described herein.

As noted herein, a variety of instruments and devices can be used in conjunction with the systems and methods described herein. In one embodiment, for example, an angled coil sensor 1031 is employed during the targeted navigation. In accordance with this embodiment, for example, instead of using a conventional wire sensor 1030, as shown in FIG. 21A, wrapped at about a 90° angle (i.e., roughly perpendicular) to the axial length (or core) 1032 of the sensor, the coil 1034 is wrapped at an acute angle Θ (i.e., the angle is less than about 90°) relative to the axial length 1032 of the sensor 1031, as shown in FIG. 21B. In one embodiment, the coil 1034 is positioned (e.g., wrapped) at an angle Θ of from about 30° to about 60° relative to the axial length 1032. In one preferred embodiment, the coil 1034 is positioned at about a 45° angle relative to the axial length 1032. The positioning of the coil 1034 in accordance with the exemplary embodiments described herein advantageously provides a directional vector that is not parallel with the sensor core 1032. Thus, the physical axis is different and, as the sensor moves, this additional directional vector can be quantified and used to detect up and down (and other directional) movement. This motion can be captured over time as described herein to determine orientation and prepare and display the more accurate images.

An external reference marker 22 can be placed in a location close to the region of the patient where the procedure is to be performed, yet in a stable location that will not move (or that will move a negligible amount) with the patient's heart beat and respiration. If patient 10 is securely fixed to table 12 for the procedure, external reference marker 22 (which may be described as "static") can be affixed to table 12. If patient 10 is not completely secured to table 12, external reference marker 22 can be placed on region of the back of patient 10 exhibiting the least amount of movement. Tracker 20 can be configured to track external reference marker 22.

One or more non-tissue internal reference markers 24 can be placed in the gross region where the image guided navigation will be carried out. Non-tissue internal reference marker(s) 24 should be placed in an anatomic location that exhibits movement that is correlated with the movement of the anatomy intended for image guided navigation. This location will be internal to the patient, in the gross location of the anatomy of interest.

Medical instrument 16, instrument reference marker(s) 18, external reference marker 22, and non-tissue internal reference marker(s) 24 can be coupled to converter 26 of system 100. Converter 26, one example of which may be referred to in the art as a break-out box, can be configured to convert analog measurements received from the reference markers and tracker 20 into digital data understandable by image guidance computing platform 30, and relay that data to image guidance computing platform 30 to which converter 26 can be coupled. Image guidance computing platform 30 can take the form of a computer, and may include a monitor on which a representation of one or more instruments used during the IGI can be displayed over an image of the anatomy of interest.

System 100 also includes a periodic human characteristic signal monitor, such as ECG monitor 32, which can be configured to receive a periodic human characteristic signal. For example, ECG monitor 32 can be configured to receive an ECG signal in the form of the ECG data transmitted to it by ECG leads 34 coupled to patient 10. The periodic human characteristic signal monitor (e.g., ECG monitor 32) can also be configured to relay a periodic human characteristic signal (e.g., ECG data) to image guidance computing platform 30, to which it can be coupled.

Prior to the start of the image guided intervention, non-tissue internal reference marker(s) 24—but not necessarily static external reference marker 22—should be placed in the gross region of interest for the procedure. After placement of non-tissue internal reference marker(s) 24, patient 10 is to be scanned with an imaging device, such as gated scanner 40, and the resulting gated image dataset transferred to image guidance computing platform 30, to which the imaging device is coupled and which can reside in the operating or procedure theatre. Examples of suitable imaging devices, and more specifically suitable gated scanners, include ECG-gated MRI scanners and ECG-gated CT scanners. A hospital network 50 may be used to couple gated scanner 40 to image guidance computing platform 30.

The imaging device (e.g., gated scanner 40) can be configured to create a gated dataset that includes pre-operative images, one or more of which (up to all) are taken using the imaging device and are linked to a sample of a periodic human characteristic signal (e.g., a sample, or a phase, of an ECG signal). Once patient 10 is scanned using the imaging device and the gated dataset is transferred to and received by image guidance computing platform 30, patient 10 can be secured to operating table 12 and the equipment making up system 100 (e.g., tracker 20, converter 26, image guidance computing platform 30, ECG monitor 32, and gated scanner 40) set up as shown in FIG. 8. Information can then flow among the system 100 components.

Figure 9:
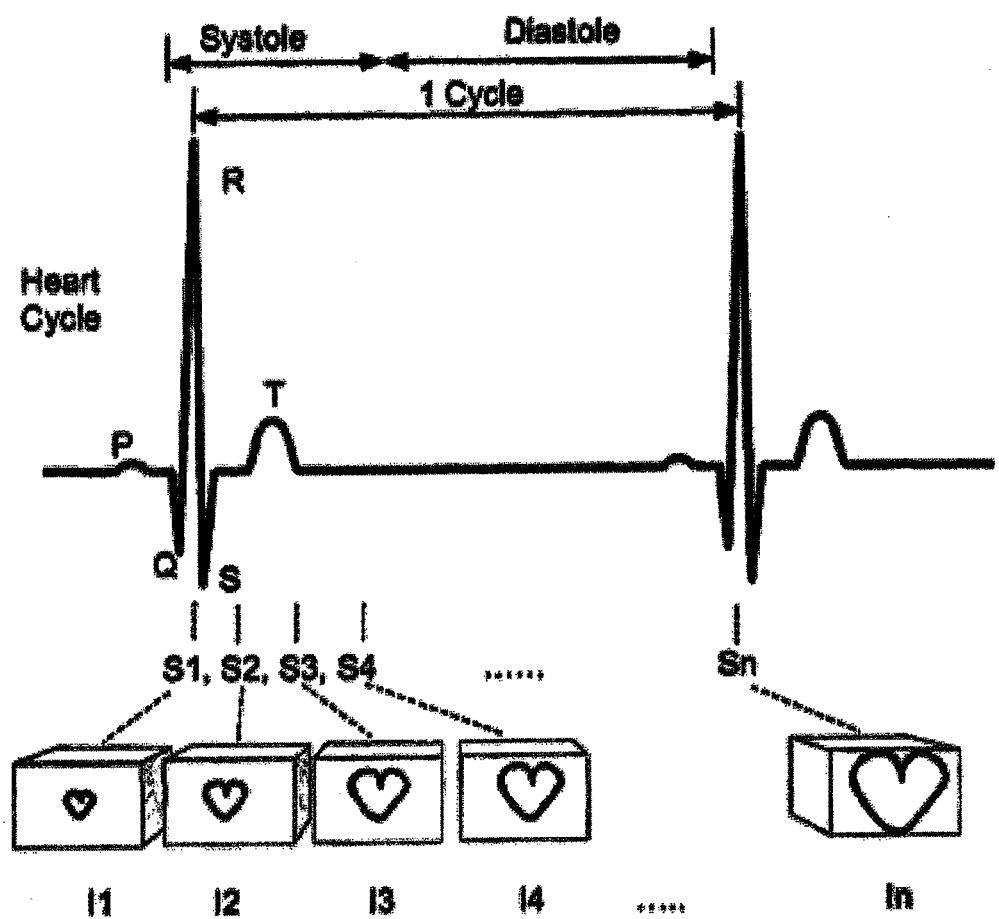
FIG. 9 illustrates one example of samples of a periodic human characteristic signal (specifically, an ECG waveform) associated, or gated, with images of dynamic anatomy.

At this point, a gated dataset created by gated scanner 40 resides on image guidance computing platform 30. FIG. 9 highlights the relationship between the samples (S1 . . . Sn) and the images (I1 . . . In) that were captured by gated scanner 40. Designations P, Q, R, S, and T are designations well known in the art; they designate depolarizations and re-polarizations of the heart. Gated scanner 40 essentially creates an image of the anatomy of interest at a particular instant in time during the anatomy's periodic movement. Image I1 corresponds to the image that was captured at the S1 moment of patient's 10 ECG cycle. Similarly, I2 is correlated with S2, and In with Sn.

Figure 10:
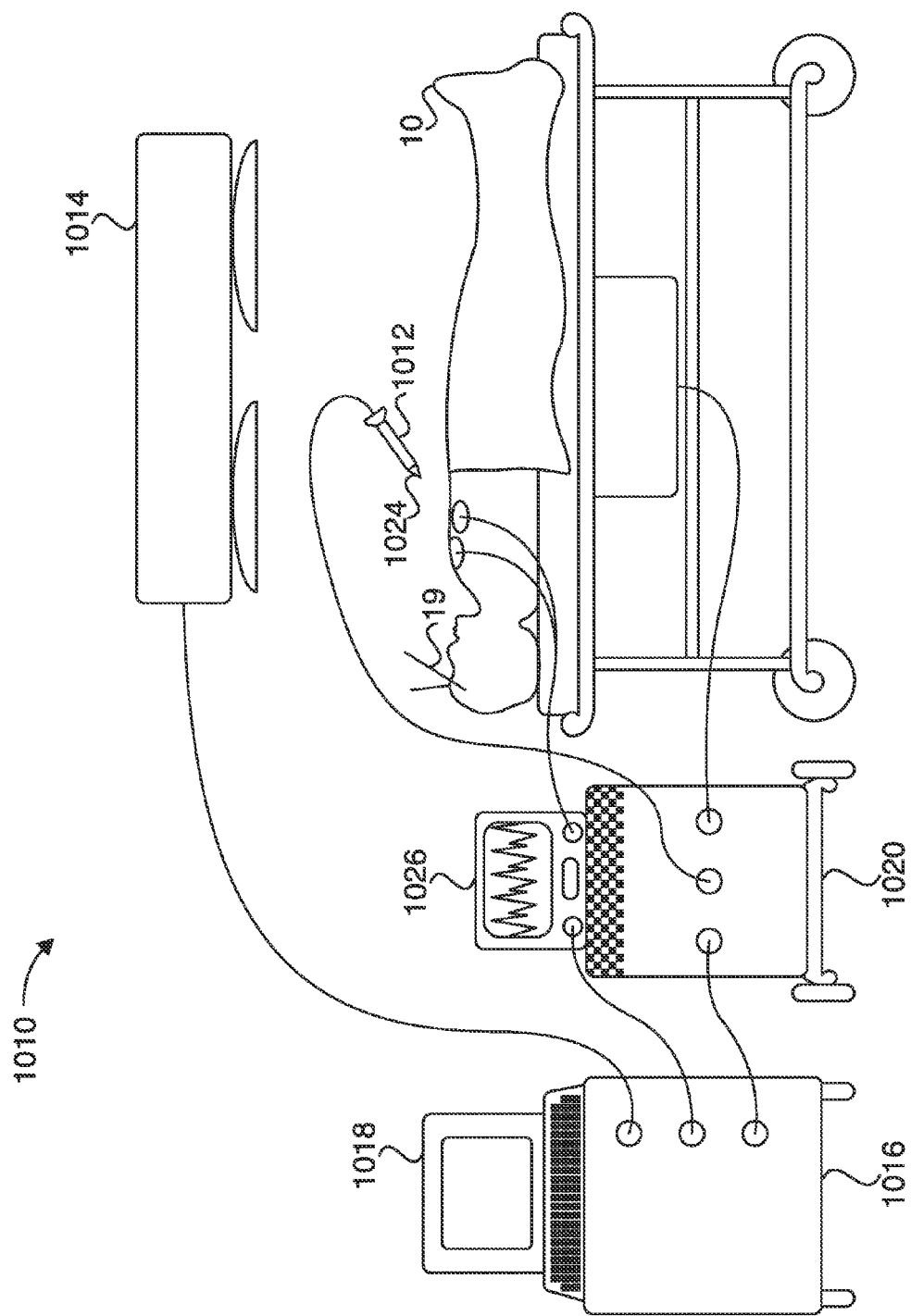
FIG. 10 is a diagram of an exemplary surgical instrument navigation system in accordance with present invention.

FIG. 10 is a diagram of another exemplary surgical instrument navigation system 1010. In accordance with one aspect of the present invention, the surgical instrument navigation system 1010 is operable to visually simulate a virtual volumetric scene within the body of a patient, such as an internal body cavity, from a point of view of a surgical instrument 1012 residing in the cavity of a patient 10. To do so, the surgical instrument navigation system 1010 is primarily comprised of a surgical instrument 1012, a data processor 1016 having a display 1018, and a tracking subsystem 1020. The surgical instrument navigation system 1010 may further include (or accompanied by) an imaging device 1014 that is operable to provide image data to the system.

The surgical instrument 1012 is preferably a relatively inexpensive, flexible and/or steerable catheter that may be of a disposable type. The surgical instrument 1012 is modified to include one or more tracking sensors 1024 that are detectable by the tracking subsystem 1020. It is readily understood that other types of surgical instruments (e.g., a guide wire, a needle, a forcep, a pointer probe, a stent, a seed, an implant, an endoscope, an energy delivery device, a therapy delivery device, etc.) are also within the scope of the present invention. It is also envisioned that at least some of these surgical instruments may be wireless or have wireless communications links. It is also envisioned that the surgical instruments may encompass medical devices which are used for exploratory purposes, testing purposes or other types of medical procedures.

Figure 11:
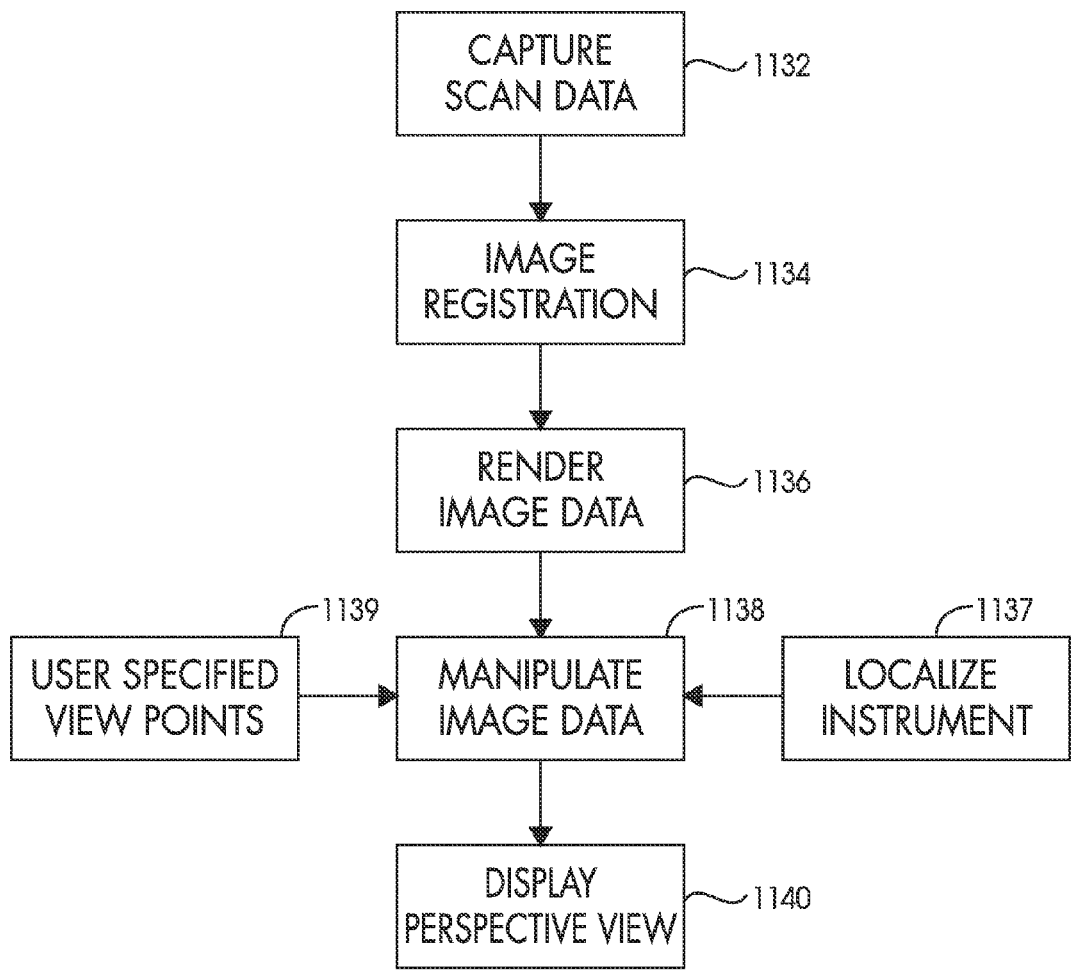
FIG. 11 is a flowchart that depicts a technique for simulating a virtual volumetric scene of a body cavity from a point of view of a surgical instrument positioned within the patient in accordance with the present invention.

Referring to FIG. 11, the imaging device 1014 is used to capture volumetric scan data 1132 representative of an internal region of interest within the patient 10. The three-dimensional scan data is preferably obtained prior to surgery on the patient 10. In this case, the captured volumetric scan data may be stored in a data store associated with the data processor 1016 for subsequent processing. However, one skilled in the art will readily recognize that the principles of the present invention may also extend to scan data acquired during surgery. It is readily understood that volumetric scan data may be acquired using various known medical imaging devices 1014, including but not limited to a magnetic resonance imaging (MRI) device, a computed tomography (CT) imaging device, a positron emission tomography (PET) imaging device, a 2D or 3D fluoroscopic imaging device, and 2D, 3D or 4D ultrasound imaging devices. In the case of a two-dimensional ultrasound imaging device or other two-dimensional image acquisition device, a series of two-dimensional data sets may be acquired and then assembled into volumetric data as is well known in the art using a two-dimensional to three-dimensional conversion.

The multi-dimensional imaging modalities described herein may also be coupled with digitally reconstructed radiography (DRR) techniques. In accordance with a fluoroscopic image acquisition, for example, radiation passes through a physical media to create a projection image on a radiation-sensitive film or an electronic image intensifier. Given a 3D or 4D dataset as described herein, for example, a simulated image can be generated in conjunction with DRR methodologies. DRR is generally known in the art, and is described, for example, by Lemieux et al. (Med. Phys. 21(11), November 1994, pp. 1749-60).

Figure 17:
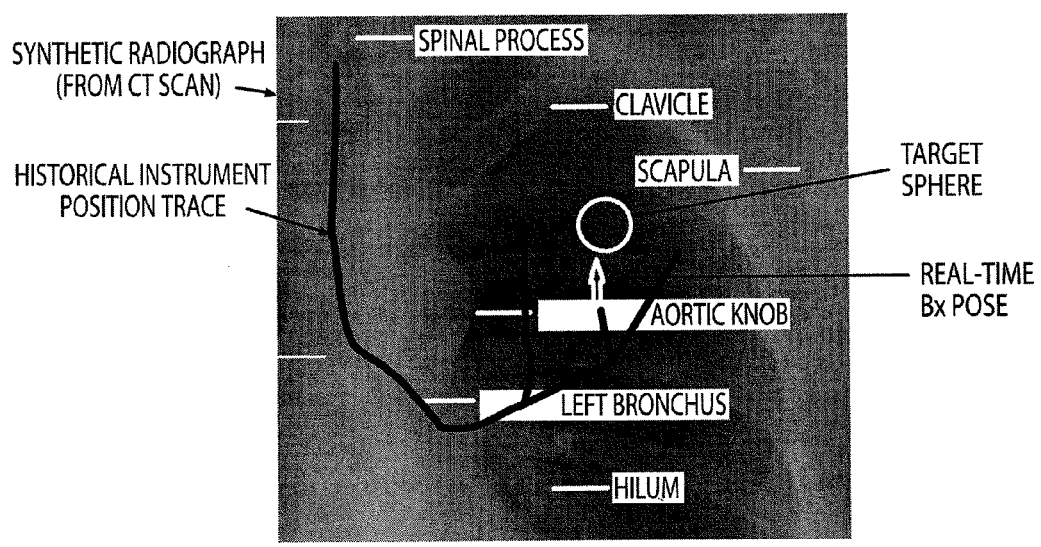
FIG. 17 is an image of an exemplary synthetic radiograph in accordance with the present invention, depicting the historical instrument position trace.

When a DRR image is created, a fluoroscopic image is formed by computationally projecting volume elements, or voxels, of the 3D or 4D dataset onto one or more selected image planes. Using a 3D or 4D dataset of a given patient as described herein, for example, it is possible to generate a DRR image that is similar in appearance to a corresponding patient image. This similarity can be due, at least in part, to similar intrinsic imaging parameters (e.g., projective transformations, distortion corrections, etc.) and extrinsic imaging parameters (e.g., orientation, view direction, etc.). The intrinsic imaging parameters can be derived, for instance, from the calibration of the equipment. Advantageously, this provides another method to see the up-and-down (and other directional) movement of the instrument. This arrangement further provides the ability to see how the device moves in an image (s), which translates to improved movement of the device in a patient. An exemplary pathway in accordance with the disclosure herein can be seen in FIG. 17.

A dynamic reference frame 19 is attached to the patient proximate to the region of interest within the patient 10. To the extent that the region of interest is a vessel or a cavity within the patient, it is readily understood that the dynamic reference frame 19 may be placed within the patient 10. To determine its location, the dynamic reference frame 19 is also modified to include tracking sensors detectable by the tracking subsystem 1020. The tracking subsystem 1020 is operable to determine position data for the dynamic reference frame 19 as further described below.

The volumetric scan data is then registered as shown at 1134. Registration of the dynamic reference frame 19 generally relates information in the volumetric scan data to the region of interest associated with the patient. This process is referred to as registering image space to patient space. Often, the image space must also be registered to another image space. Registration is accomplished through knowledge of the coordinate vectors of at least three non-collinear points in the image space and the patient space.

Registration for image guided surgery can be completed by different known techniques. First, point-to-point registration is accomplished by identifying points in an image space and then touching the same points in patient space. These points are generally anatomical landmarks that are easily identifiable on the patient. Second, surface registration involves the user's generation of a surface in patient space by either selecting multiple points or scanning, and then accepting the best fit to that surface in image space by iteratively calculating with the data processor until a surface match is identified. Third, repeat fixation devices entail the user repeatedly removing and replacing a device (i.e., dynamic reference frame, etc.) in known relation to the patient or image fiducials of the patient. Fourth, automatic registration by first attaching the dynamic reference frame to the patient prior to acquiring image data. It is envisioned that other known registration procedures are also within the scope of the present invention, such as that disclosed in U.S. Pat. No. 6,470,207, filed on Mar. 23, 1999, entitled "NAVIGATIONAL GUIDANCE VIA COMPUTER-ASSISTED FLUOROSCOPIC IMAGING", which is hereby incorporated by reference.

Figure 12:
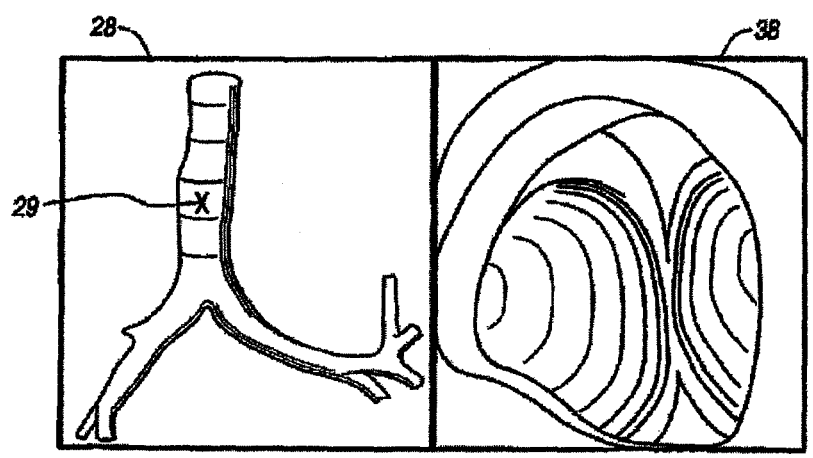
FIG. 12 is an exemplary display from the surgical instrument navigation system of the present invention.

FIG. 12 illustrates another type of secondary image 28 which may be displayed in conjunction with the primary perspective image 38. In this instance, the primary perspective image is an interior view of an air passage within the patient 10. The secondary image 28 is an exterior view of the air passage which includes an indicia or graphical representation 29 that corresponds to the location of the surgical instrument 1012 within the air passage. In FIG. 12, the indicia 29 is shown as a crosshairs. It is envisioned that other indicia may be used to signify the location of the surgical instrument in the secondary image. As further described below, the secondary image 28 is constructed by superimposing the indicia 29 of the surgical instrument 1012 onto the manipulated image data 1138 (see FIG. 11).

Figure 13:
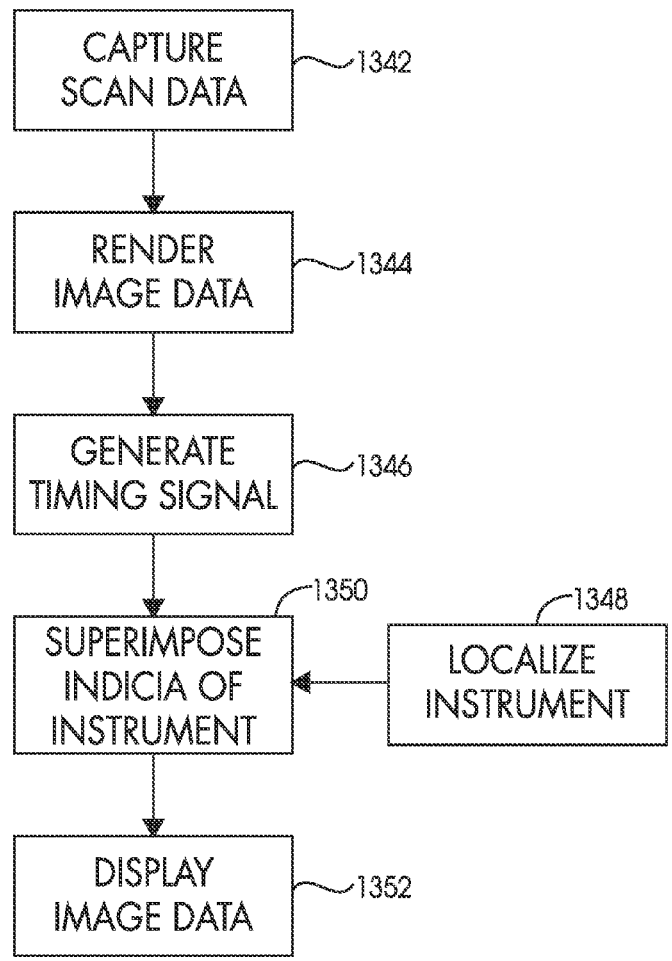
FIG. 13 is a flowchart that depicts a technique for synchronizing the display of an indicia or graphical representation of the surgical instrument with cardiac or respiratory cycle of the patient in accordance with the present invention.

Referring to FIG. 13, the display of an indicia of the surgical instrument 1012 on the secondary image may be synchronized with an anatomical function, such as the cardiac or respiratory cycle, of the patient. In certain instances, the cardiac or respiratory cycle of the patient may cause the surgical instrument 1012 to flutter or jitter within the patient. For instance, a surgical instrument 1012 positioned in or near a chamber of the heart will move in relation to the patient's heart beat. In these instance, the indicia of the surgical instrument 1012 will likewise flutter or jitter on the displayed image 1140. It is envisioned that other anatomical functions which may effect the position of the surgical instrument 1012 within the patient are also within the scope of the present invention.

To eliminate the flutter of the indicia on the displayed image 1140, position data for the surgical instrument 1012 is acquired at a repetitive point within each cycle of either the cardiac cycle or the respiratory cycle of the patient. As described above, the imaging device 1014 is used to capture volumetric scan data 1342 representative of an internal region of interest within a given patient. A secondary image may then be rendered 1344 from the volumetric scan data by the data processor 1016.

In order to synchronize the acquisition of position data for the surgical instrument 1012, the surgical instrument navigation system 1010 may further include a timing signal generator 1026. The timing signal generator 1026 is operable to generate and transmit a timing signal 1346 that correlates to at least one of (or both) the cardiac cycle or the respiratory cycle of the patient 10. For a patient having a consistent rhythmic cycle, the timing signal might be in the form of a periodic clock signal. Alternatively, the timing signal may be derived from an electrocardiogram signal from the patient 10. One skilled in the art will readily recognize other techniques for deriving a timing signal that correlate to at least one of the cardiac or respiratory cycle or other anatomical cycle of the patient.

As described above, the indicia of the surgical instrument 1012 tracks the movement of the surgical instrument 1012 as it is moved by the surgeon within the patient 10. Rather than display the indicia of the surgical instrument 1012 on a real-time basis, the display of the indicia of the surgical instrument 1012 is periodically updated 1348 based on the timing signal from the timing signal generator 1026. In one exemplary embodiment, the timing generator 1026 is electrically connected to the tracking subsystem 1020. The tracking subsystem 1020 is in turn operable to report position data for the surgical instrument 1012 in response to a timing signal received from the timing signal generator 1026. The position of the indicia of the surgical instrument 1012 is then updated 1350 on the display of the image data. It is readily understood that other techniques for synchronizing the display of an indicia of the surgical instrument 1012 based on the timing signal are within the scope of the present invention, thereby eliminating any flutter or jitter which may appear on the displayed image 1352. It is also envisioned that a path (or projected path) of the surgical instrument 1012 may also be illustrated on the displayed image data 1352.

Figure 14:
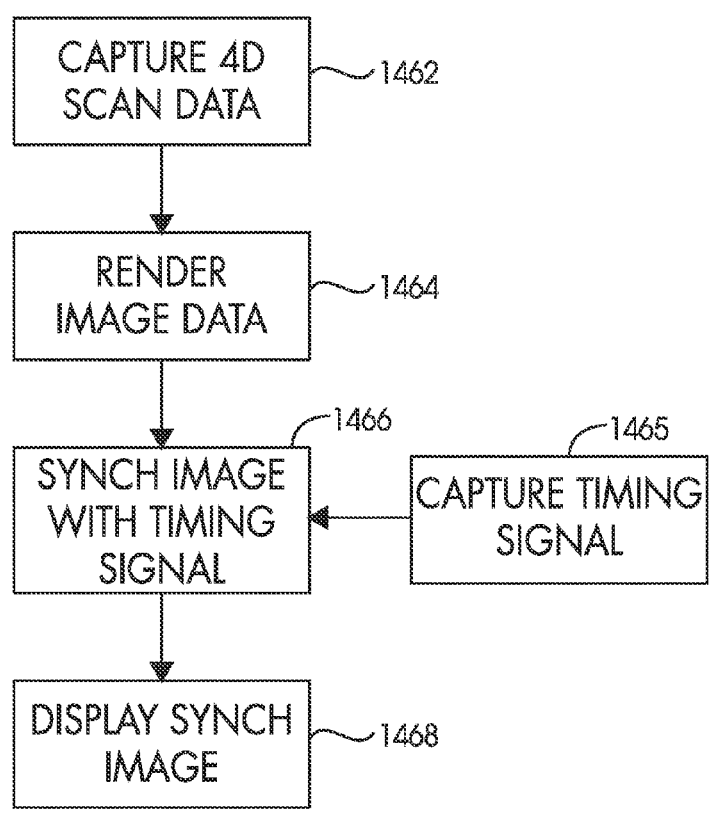
FIG. 14 is a flowchart that depicts a technique for generating four-dimensional image data that is synchronized with the patient in accordance with the present invention.
Figure 15:
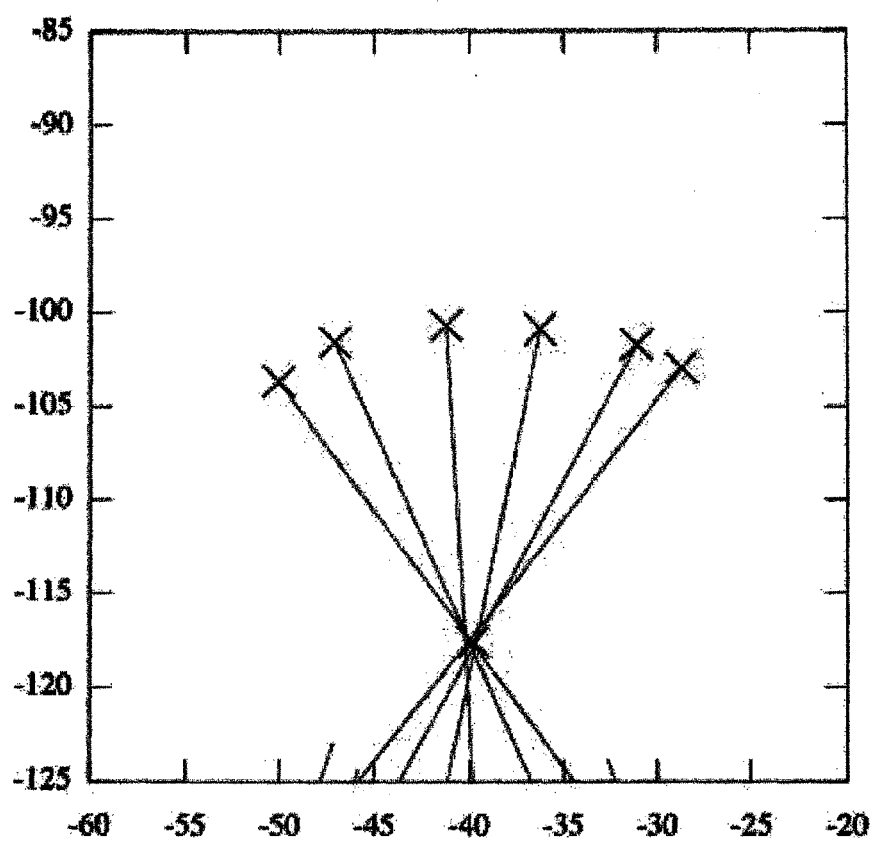
FIG. 15 is a graph depicting an axis or point that the instrument (e.g., a bronchoscope) deflects in a single planar direction. The graph shows the instrument (e.g., a bronchoscope) being maneuvered in six different orientations in a 3D localizer volume, with all orientations converging about a common axis or point of deflection.
Figure 16:
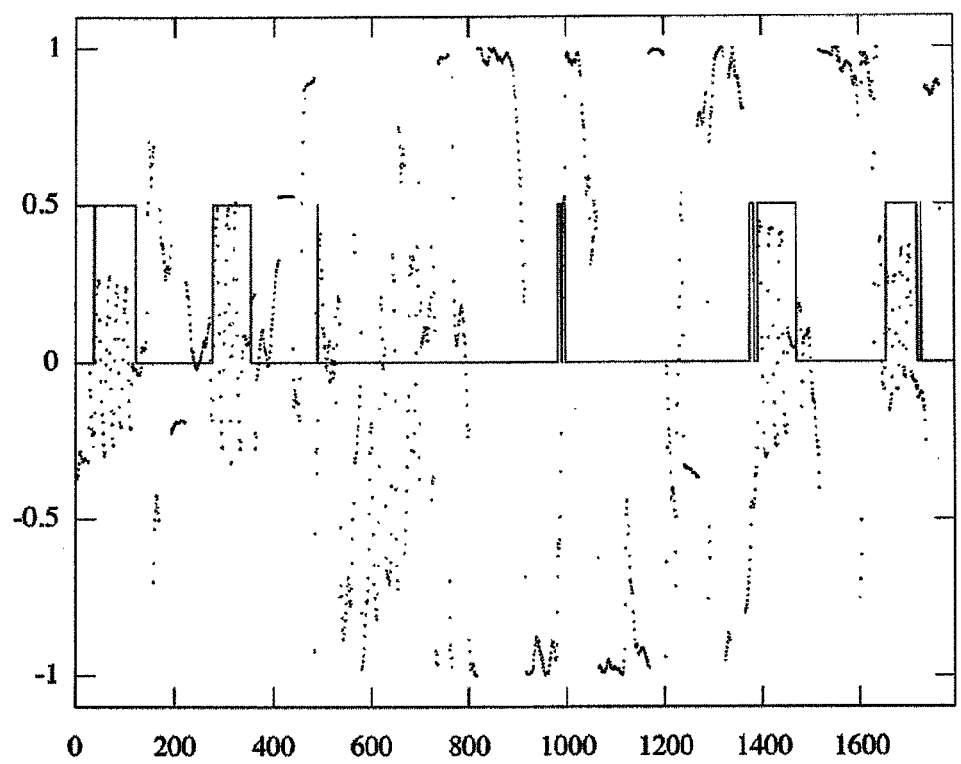
FIG. 16 is a graph depicting the eigenvalues (e0,e1,e2) for a moving 3.0 sec PCA (principal component analysis) window over a data file including 1800 samples. The square wave represents an on/off "wiggle detector" state based on the algorithm described herein, and this square wave demonstrates that the algorithm exhibits no false negatives for the validation test data and that the seven exemplary "wiggle" periods are clearly matched to the "on" state of the wiggle detector. The implementation of the algorithm uses low pass filtering and an appropriate comparator function to eliminate any false positive traces or spots ("blips") indicated in FIG. 16.

In another aspect of the present invention, the surgical instrument navigation system 1010 may be further adapted to display four-dimensional image data for a region of interest as shown in FIG. 14. In this case, the imaging device 1014 is operable to capture volumetric scan data 1462 for an internal region of interest over a period of time, such that the region of interest includes motion that is caused by either the cardiac cycle or the respiratory cycle of the patient 10. A volumetric perspective view of the region may be rendered 1464 from the volumetric scan data 1462 by the data processor 1016 as described above. The four-dimensional image data may be further supplemented with other patient data, such as temperature or blood pressure, using coloring coding techniques.

In order to synchronize the display of the volumetric perspective view in real-time with the cardiac or respiratory cycle of the patient, the data processor 1016 is adapted to receive a timing signal from the timing signal generator 1026. As described above, the timing signal generator 1026 is operable to generate and transmit a timing signal that correlates to either the cardiac cycle or the respiratory cycle of the patient 10. In this way, the volumetric perspective image may be synchronized 1466 with the cardiac or respiratory cycle of the patient 10. The synchronized image 1466 is then displayed 1468 on the display 1018 of the system. The four-dimensional synchronized image may be either (or both of) the primary image rendered from the point of view of the surgical instrument or the secondary image depicting the indicia of the position of the surgical instrument 1012 within the patient 10. It is readily understood that the synchronization process is also applicable to two-dimensional image data acquire over time.

To enhance visualization and refine accuracy of the displayed image data, the surgical navigation system can use prior knowledge such as the segmented vessel or airway structure to compensate for error in the tracking subsystem or for inaccuracies caused by an anatomical shift occurring since acquisition of scan data. For instance, it is known that the surgical instrument 1012 being localized is located within a given vessel or airway and, therefore should be displayed within the vessel or airway. Statistical methods can be used to determine the most likely location; within the vessel or airway with respect to the reported location and then compensate so the display accurately represents the instrument 1012 within the center of the vessel or airway. The center of the vessel or airway can be found by segmenting the vessels or airways from the three-dimensional datasets and using commonly known imaging techniques to define the centerline of the vessel or airway tree. Statistical methods may also be used to determine if the surgical instrument 1012 has potentially punctured the vessel or airway. This can be done by determining the reported location is too far from the centerline or the trajectory of the path traveled is greater than a certain angle (worse case 90 degrees) with respect to the vessel or airway. Reporting this type of trajectory (error) is very important to the clinicians. The tracking along the center of the vessel may also be further refined by correcting for motion of the respiratory or cardiac cycle, as described above. While navigating along the vessel or airway tree prior knowledge about the last known location can be used to aid in determining the new location. The instrument or navigated device must follow a pre-defined vessel or airway tree and therefore cannot jump from one branch to the other without traveling along a path that would be allowed. The orientation of the instrument or navigated device can also be used to select the most likely pathway that is being traversed. The orientation information can be used to increase the probability or weight for selected location or to exclude potential pathways and therefore enhance system accuracy.

The surgical instrument navigation system of the present invention may also incorporate atlas maps. It is envisioned that three-dimensional or four-dimensional atlas maps may be registered with patient specific scan data or generic anatomical models. Atlas maps may contain kinematic information (e.g., heart and lung models) that can be synchronized with four-dimensional image data, thereby supplementing the real-time information. In addition, the kinematic information may be combined with localization information from several instruments to provide a complete four-dimensional model of organ motion. The atlas maps may also be used to localize bones or soft tissue which can assist in determining placement and location of implants.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable any person skilled in the art to make or use the invention. While the invention has been particularly shown and described with reference to embodiments thereof, it will be understood by those skilled in art that various changes in form and details may be made therein without departing from the spirit and scope of the invention. For example, the PTD, markers and localization elements can be constructed from any suitable material, and can be a variety of different shapes and sizes, not necessarily specifically illustrated, while still remaining within the scope of the invention.

What is claimed is:

1. An image-guided method comprising:
   directing an endoscope comprising a five degree of freedom tip sensor to an anatomical position in a patient;
   capturing video of the patient's anatomy with the endoscope,
   aligning the captured video with a visual orientation of a user directing the endoscope to the anatomical position;
   activating a steering mechanism of the endoscope to repeatedly move the tip sensor in an arc constrained to a plane;
   determining the orientation and location of the tip sensor in the patient as the tip sensor is being repeatedly moved;
   defining a sixth degree of freedom of the tip sensor using the determined orientation and location of the tip sensor; and
   correlating the determined tip sensor location and orientation with one or more patient images acquired prior to the repeated movement of the tip sensor.

2. The image-guided method of claim 1 wherein the anatomical position is a branching point of a bronchial tree.

3. The image-guided method of claim 1 wherein the tip sensor is an angled coil sensor, the coil being disposed at a 45° angle relative to a core portion of the tip sensor.

4. The image-guided method of claim 1 wherein orientation and location determination comprise applying a deformation vector field.

5. The image-guided method of claim 1 wherein the one or more patient images are derived from an imaging device in conjunction with a patient tracking device disposed at an external region of the patient.

* * * * *